US008296108B2

(12) United States Patent  (10) Patent No.: US 8,296,108 B2
Tanaka  (45) Date of Patent: Oct. 23, 2012

(54) TIME SERIES DATA ANALYZER, AND A COMPUTER-READABLE RECORDING MEDIUM RECORDING A TIME SERIES DATA ANALYSIS PROGRAM

(75) Inventor: Yukio Tanaka, Tokyo (JP)

(73) Assignee: Yugen Kaisha Suwa Torasuto, Tokyo (JP)

( * ) Notice: Subject to any disclaimer, the term of this patent is extended or adjusted under 35 U.S.C. 154(b) by 385 days.

(21) Appl. No.: 12/753,457

(22) Filed: Apr. 2, 2010

(65) Prior Publication Data

US 2011/0246144 A1  Oct. 6, 2011

(51) Int. Cl.
| G06F 7/60 | (2006.01) |
| G06F 9/44 | (2006.01) |
| G06F 11/30 | (2006.01) |
| G06G 7/58 | (2006.01) |
| G06E 1/00 | (2006.01) |
| A61M 21/00 | (2006.01) |
| A61B 5/00 | (2006.01) |

(52) U.S. Cl. ............... 703/2; 703/11; 600/27; 600/300; 600/301; 600/323; 600/428; 600/431; 600/483; 600/500; 600/509; 600/544; 607/40; 607/45; 702/183; 702/186; 702/189; 702/191; 706/20; 706/52

(58) Field of Classification Search .................... 600/27, 600/300, 301, 323, 428, 431, 483, 500, 504, 600/508, 509, 544; 607/40, 45; 702/183, 702/186, 189, 191; 706/20, 52; 703/2, 11
See application file for complete search history.

(56) References Cited

U.S. PATENT DOCUMENTS

| 4,960,129 | A | * | 10/1990 | dePaola et al. | 600/508 |
| 5,213,106 | A | * | 5/1993 | Lerner | 600/508 |
| 5,222,503 | A | * | 6/1993 | Ives et al. | 600/544 |
| 5,299,119 | A | * | 3/1994 | Kraf et al. | 600/509 |
| 5,311,876 | A | * | 5/1994 | Olsen et al. | 600/544 |
| 5,349,962 | A | * | 9/1994 | Lockard et al. | 600/545 |
| 5,623,925 | A | * | 4/1997 | Swenson et al. | 600/301 |
| 5,732,158 | A | * | 3/1998 | Jaenisch | 382/249 |
| 5,815,413 | A | * | 9/1998 | Hively et al. | 702/191 |
| 5,967,981 | A | * | 10/1999 | Watrous | 600/428 |
| 5,995,868 | A | * | 11/1999 | Dorfmeister et al. | 600/544 |

(Continued)

OTHER PUBLICATIONS

Casdagli et al. "Characterizing nonlinearity in invasive EEG recordings from temporal lobe epilepsy", 1996.*

(Continued)

*Primary Examiner* — Shambhavi Patel
(74) *Attorney, Agent, or Firm* — Wenderoth, Lind & Ponack, L.L.P.

(57) ABSTRACT

A time series data analyzer includes a segment condition input section, an analysis condition input section, and an optimum condition deriving section for analyzing all segments based on the segment conditions and analysis conditions inputted in the respective input sections, under all analysis conditions by a maximum entropy method and a nonlinear least squares method. The time series data analyzer derives the optimum segment length and the optimum lag value in correspondence to selected results, and an analysis execution section executes analysis by the maximum entropy method by setting the optimum analysis conditions derived as described above. The trending of the spectrum of electroencephalogram data is used as an indicator of the state of the subject based on the findings that the spectrum of electroencephalogram data is an exponential spectrum and the gradient changes depending on the state of the subject.

20 Claims, 14 Drawing Sheets

U.S. PATENT DOCUMENTS

| | | | | |
|---|---|---|---|---|
| 6,021,345 | A * | 2/2000 | Karagueuzian et al. | 600/518 |
| 6,052,334 | A * | 4/2000 | Brumley et al. | 367/90 |
| 6,094,593 | A * | 7/2000 | Karagueuzian et al. | 600/518 |
| 6,144,877 | A * | 11/2000 | DePetrillo | 600/515 |
| 6,230,049 | B1 * | 5/2001 | Fischell et al. | 600/544 |
| 6,282,151 | B1 * | 8/2001 | Brumley et al. | 367/90 |
| 6,549,804 | B1 * | 4/2003 | Osorio et al. | 600/544 |
| 6,658,287 | B1 * | 12/2003 | Litt et al. | 600/544 |
| 6,684,234 | B1 * | 1/2004 | Kraker | 708/322 |
| 6,700,834 | B2 * | 3/2004 | Brumley et al. | 367/90 |
| 6,721,719 | B1 * | 4/2004 | Aggarwal et al. | 706/20 |
| 6,731,972 | B2 * | 5/2004 | Meyer et al. | 600/509 |
| 6,793,670 | B2 * | 9/2004 | Osorio et al. | 607/113 |
| 6,920,349 | B2 * | 7/2005 | Schreck | 600/512 |
| 6,993,458 | B1 * | 1/2006 | Castelli et al. | 702/186 |
| 7,015,701 | B2 * | 3/2006 | Wiegand et al. | 324/603 |
| 7,020,521 | B1 * | 3/2006 | Brewer et al. | 607/14 |
| 7,079,888 | B2 * | 7/2006 | Oung et al. | 600/513 |
| 7,139,677 | B2 * | 11/2006 | Hively | 702/183 |
| 7,269,455 | B2 * | 9/2007 | Pineda | 600/544 |
| 7,277,758 | B2 * | 10/2007 | DiLorenzo | 607/45 |
| 7,280,867 | B2 * | 10/2007 | Frei et al. | 600/544 |
| 7,317,660 | B2 * | 1/2008 | Brumle et al. | 367/90 |
| 7,372,047 | B2 * | 5/2008 | Sato et al. | 250/491.1 |
| 7,392,079 | B2 * | 6/2008 | Donoghue et al. | 600/545 |
| 7,461,045 | B1 * | 12/2008 | Chaovalitwongse et al. | 706/45 |
| 7,499,752 | B2 * | 3/2009 | Maschino et al. | 607/40 |
| 7,532,935 | B2 * | 5/2009 | Maschino et al. | 607/45 |
| 7,610,083 | B2 * | 10/2009 | Drew et al. | 600/509 |
| 7,623,928 | B2 * | 11/2009 | DiLorenzo | 607/45 |
| 7,640,055 | B2 * | 12/2009 | Geva et al. | 600/544 |
| 7,668,579 | B2 * | 2/2010 | Lynn | 600/323 |
| 7,672,717 | B1 * | 3/2010 | Zikov et al. | 600/544 |
| 7,706,852 | B2 * | 4/2010 | Baker, Jr. | 600/323 |
| 7,747,325 | B2 * | 6/2010 | Dilorenzo | 607/45 |
| 7,761,145 | B2 * | 7/2010 | Virag et al. | 600/544 |
| 7,761,146 | B2 * | 7/2010 | Carlson et al. | 600/544 |
| 7,765,088 | B2 * | 7/2010 | Drew | 702/189 |
| 7,803,118 | B2 * | 9/2010 | Reisfeld et al. | 600/483 |
| 7,860,561 | B1 * | 12/2010 | Modarres | 600/544 |
| 7,937,138 | B2 * | 5/2011 | Liley | 600/544 |
| 7,962,214 | B2 * | 6/2011 | Byerman et al. | 607/40 |
| 7,976,465 | B2 * | 7/2011 | Frei et al. | 600/301 |
| 8,024,032 | B1 * | 9/2011 | Osorio et al. | 600/545 |
| 8,036,736 | B2 * | 10/2011 | Snyder et al. | 600/544 |
| 8,137,269 | B2 * | 3/2012 | Sheikhzadeh-Nadjar et al. | 600/300 |
| 8,137,270 | B2 * | 3/2012 | Keenan et al. | 600/301 |
| 8,152,732 | B2 * | 4/2012 | Lynn et al. | 600/529 |
| 2003/0105409 | A1 * | 6/2003 | Donoghue et al. | 600/545 |
| 2006/0247542 | A1 * | 11/2006 | Watanabe et al. | 600/500 |
| 2007/0255135 | A1 * | 11/2007 | Kalafut et al. | 600/431 |
| 2007/0260151 | A1 * | 11/2007 | Clifford | 600/509 |
| 2008/0033254 | A1 * | 2/2008 | Kamath et al. | 600/300 |
| 2008/0039737 | A1 * | 2/2008 | Breiter et al. | 600/544 |
| 2008/0071136 | A1 * | 3/2008 | Oohashi et al. | 600/27 |
| 2009/0054800 | A1 * | 2/2009 | Martinerie et al. | 600/544 |
| 2009/0076403 | A1 * | 3/2009 | Hopenfeld | 600/516 |
| 2009/0076404 | A1 * | 3/2009 | Hopenfeld | 600/521 |
| 2009/0292180 | A1 * | 11/2009 | Mirow | 600/301 |
| 2012/0004561 | A1 * | 1/2012 | John | 600/504 |

OTHER PUBLICATIONS

Bagarinao et al. "Algorithm for Vector Autoregressive Model Parameter Estimation Using an Orthogonalization Procedure", Annals of Biomedical Engineering, vol. 30, pp. 260-271, 2002.*

Becker et al. "Anaesthesia Monitoring by Recurrence Quantification Analysis of EEG Data", 2010.*

Cong et al. "Empirical Mode Decomposition on Mismatch Negativity", 2008.*

Fanizza et al. "Spectral estimation by least-squares optimization based on rational covariance extension", Automatica 43 (2007) 362-370.*

Ghil et al. "Advanced Spectral Analysis Methods", 2007.*

Ghil et al. "Advanced Spectral Methods for Climatic Time Series", Reviews of Geophysics, 40, Mar. 1, 2002.*

Golub et al. "Separable Nonlinear Least Squares: the Variable Projection Method and its Applications", 2002.*

Jahromi et al. "Spectrum Estimation Using Multirate Observations", IEEE Transactions on Signal Processing, 2003.*

Li et al. "Measure of the electroencephalographic effects of sevoflurane using recurrence dynamics", Neuroscience Letters 424 (2007) 47-50.*

Markovic et al. "Sensitivity of Hurst parameter estimation to periodic signals in time series and Filtering approaches", 2005.*

Nielson, Finn. "Neuroinformatics in Functional Neuroimaging", 2002.*

Palacin et al. "Suboptimal Filtering and Nonlinear Time Scale Transformation for the Analysis of Multiexponential Decays", IEEE Transactions on Instrumentation and Measurement, vol. 50, No. 1, Feb. 2001.*

Pflieger et al. "Nonlinear Analysis of Multimodal Dynamic Brain Imaging Data", 2001.*

Subha et al. "EEG Signal Analysis: A Survey", J Med Syst (2010) 34:195-212.*

Tarvainen et al. "Kubios HRV Analysis: User's Guide", 2005.*

Terachi et al. "Detailed Study of Temporal Variations of EEG by Improved MEM Spectral Analysis With High Resolution Power", International Symposium on Signal Processing and its Applications (ISSPA)), Aug. 13-16, 2001.*

Wu et al. "Intelligent Artefact Identification in Electroencephalography Signal Processing", 2004.*

Zbilut et al. "Recurrence quantification analysis as a tool for nonlinear exploration of nonstationary cardiac signals", Medical Engineering & Physics 24 (2002) 53-60.*

Broerson et al. "Automatic Spectral Analysis With Time Series Models", IEEE Transactions on Instrumentation and Measurement, vol. 51, No. 2, Apr. 2002.*

Broersen, Piet. "Automatic spectral analysis with missing data", Digital Signal Processing 16 (2006) 754-766.*

* cited by examiner (a) Electroencephalogram data (b) Spectral density (a) Electroencephalogram data with a length of 5 seconds (b) Description by generalized trigonometric polynominal (without noise term)

(c) Residuals (electroencephalogram data - generalized trigonometric polynominal)

(a) Electroencephalogram data with a length of 5 seconds (b) Description by generalized trigonometric polynominal (without noise term)

(c) Residuals (electroencephalogram data - generalized trigonometric polynominal)

| (a) | | | (b) | | |
|---|---|---|---|---|---|
| [Details of respective Modes] | | | [Details of respective Modes] | | |
| Period | Amplitude | Acrotime | Period | Amplitude | Acrotime |
| 0.2000 | 10.11 | 0.05002 | 0.2000 | 10.11 | 0.05002 |
| 0.1000 | 7.11 | 0.02423 | 0.1000 | 3.62 | 0.02349 |
| 0.0667 | 4.88 | 0.04965 | 0.0667 | 4.88 | 0.04965 |
| 0.0500 | 3.20 | 0.01231 | 0.0500 | 3.20 | 0.01231 |

(a) Electroencephalogram data during rest (b) Spectral density (a) Electroencephalogram data during sound sleep (b) Spectral density (a) Eletroencephalogram data during arousal (b) Spectral density (a) Electroencephalogram data during anesthesia (b) Spectral density (a) Electroencephalogram data immediately after introduction of anesthesia (b) Spectral density (a) Electroencephalogram data during introduction of anesthesia (b) Spectral density

TIME SERIES DATA ANALYZER, AND A COMPUTER-READABLE RECORDING MEDIUM RECORDING A TIME SERIES DATA ANALYSIS PROGRAM

BACKGROUND OF THE INVENTION

1. Field of the Invention

The present invention relates to an analyzer of time series data such as electroencephalogram data and a computer-readable recording medium recording a time series data analysis program.

2. Description of the Related Art

The present inventor found that with regard to the chaotic time series following the respective nonlinear motion equations of Lorenz, Roessler and Duffing Models, all the spectra of the time series are exponential spectra, and reported the finding on a journal written in English of The Physical Society of Japan (Document 1) in 1995. The Japanese version of Document 1 is published in Document 2 in 1996.

In addition, the inventor analyzed, in the Document 1, the pulse wave (blood pressure waveform) data of one beat by the same method, and found that the spectrum of the data is an exponential spectrum, indicating the relation of physiological phenomena with chaotic characteristics. The Document 1 triggered the wide attention paid to the exponential spectra in the relation between chaotic time series and physiological phenomena, etc.

The Document 1 presents the important findings obtained for the first time by precisely calculating the spectra of chaotic time series using a highly precise general-purpose time series data analysis system, MemCalc (registered trademark) prepared by the present inventor. Thereafter, with the widespread use of the MemCalc (registered trademark) and application systems thereof, the group including the present inventor, and also many other researchers and groups have studied the features of spectra of various time series data, particularly biological time series data in detail.

In this situation, above all, the electroencephalogram data and analysis results thereof described in Document 3 are very interesting. The facts revealed by the Document 3 include that the spectrum of the electroencephalogram data measured at the scalp is an exponential spectrum in the frequency band of interest (1 to 30 Hz or 0.5 to 30 Hz), that the overall trend of the spectrum varies depending on the age and state of the subject, that the overall trend of an electroencephalogram spectrum varies in response to "the rhythm of sleep" about every one hour and a half also during sleep, and that the introduction of anesthesia also changes the overall trend of the spectrum.

Document 1

Norio OHTOMO, Kazuo TOKIWANO, Yukio TANAKA, Ayako SUMI, Saburou TERACHI and Hidetoshi KONNO, "Exponential Characteristics of Power Spectral Densities Caused by Chaotic Phenomena," Journal of the Physical Society of Japan, Vol. 64, No. 4 (1995), pages 1104-1113

Document 2

Supervised by Saichi HOSODA, Edited by Hiroshi KASANUKI and Norio OHTOMO, "New Development of Biological Time Series Data Analysis (in Japanese)," Book Publishing Committee, Hokkaido University, 25 Dec., 1996, pages 139-155

Document 3

Ayako SUMI, "Practice of Biological Time Series Data Analysis by MemCalc (in Japanese)," Published by Nihon Shuhjutsuki Jikan Igaku Kenkyukai (=Japanese Perioperative Research Organization), Mar. 10, 2001

The spectra of electroencephalogram data are exponential spectra and the overall trend of an exponential spectrum varies depending on the state of each subject. Therefore, it can be immediately expected that the value of the gradient can be used as an indicator of the state of the subject.

The inventor developed Makin (trade name) and Makin2 (trade name) as systems for simply obtaining the overall trend of exponential spectra of electroencephalograms in real time, and the systems are used in many research institutes. Therefore, various findings concerning the behavior of gradients are accumulated and reported.

However, presently the state of each subject cannot be identified yet by referring to the value of the gradient only. For example, both the overall trend of the exponential spectrum of the electroencephalogram obtained under anesthesia and the overall trend of the exponential spectrum of the electroencephalogram obtained during sound sleep are sharp, and therefore it is impossible to decide whether a person is anesthetized or is soundly sleeping, by referring to the value of the gradient only. Further, it can sometimes happen that a technician determines that subjects are in the same sleep stage, even though their electroencephalograms are greatly different in gradient. Gradients can also be greatly different from subject to subject. For widely and practically using the remarkable feature that the spectra of electroencephalogram data are exponential, any technical idea for breaking through the present situation as described above is needed.

SUMMARY OF THE INVENTION

The object of this invention is to solve the abovementioned problem.

For solving the abovementioned problem, this invention proposes a time series data analyzer for analyzing the segments obtained from time series data, comprising a segment condition input section, into which the shortest segment length, the longest segment length, and the total number of obtained segments including the shortest segment, the longest segment and the segments with different lengths ranging from the shortest segment length to the longest segment length, or each time step between the shortest segment and the longest segment are inputted as input items, an analysis condition input section, into which the minimum lag value, the maximum lag value, and the intervals for setting the series of lag values between the minimum lag value and the maximum lag value are inputted as input items, an optimum analysis condition deriving section, in which each of all the segments is analyzed on the basis of the segment conditions inputted in the segment condition input section and the analysis conditions inputted in the analysis condition input section, under all the analysis conditions by the maximum entropy method and the nonlinear least squares method, for selecting one appropriate segment and one appropriate analysis condition from all the analysis results and deriving the optimum segment length and the optimum lag value in correspondence to the selected results, and an analysis execution section, in which the optimum analysis conditions derived by the optimum analysis condition deriving section are set as analysis conditions, for executing the analysis by the maximum entropy method.

Further, this invention proposes the abovementioned time series data analyzer, wherein the optimum analysis condition deriving section comprises a setting processing means for obtaining multiple segments different in length from the time series data on the basis of the conditions inputted in the segment condition input section, to set the segments as sample segments and for reading the analysis conditions inputted in the analysis condition input section, to set the analysis conditions, a first processing means for calculating the power spectral densities for each of all the sample segments set by the setting processing means, under all analysis conditions using the maximum entropy method, a second processing means for extracting the dominant spectral peaks for the respective power spectral densities obtained by the first processing means, and calculating the respective quantities of the generalized trigonometric polynomial expressions about the sample segments from the dominant spectral peaks by the nonlinear least squares method, and a third processing means for determining the validities of the generalized trigonometric polynomial expressions obtained by the second processing means for the sample segment data and the consistencies of the generalized trigonometric polynomial expressions for the power spectral densities, to select one sample segment corresponding to the generalized trigonometric polynomial expression high in validity and consistency, for deriving the segment length and the lag value corresponding to the sample segment as the optimum segment length and the optimum lag value.

Further, this invention proposes the abovementioned time series data analyzer, wherein the second processing means extracts the number of the dominant spectral peaks, and the respective peak frequencies and peak powers of the dominant spectral peaks from the power spectral densities calculated by the first processing means, to calculate the respective quantities of the generalized trigonometric polynomial expressions by calculation of the nonlinear least squares method for minimizing the sum of squares of residuals, with the abovementioned number as the number of terms, and with the inverse numbers of the respective peak frequencies as the initial values of the periods of respective trigonometric terms, and the third processing means has a first selection function for comparing the standard deviations of the residuals in the respective quantities of the generalized trigonometric polynomial expressions concerning the respective sample segments, with a set value, to reject the generalized trigonometric polynomial expressions, the standard deviations of which are not lower than the set value and to retain the other generalized trigonometric polynomial expressions as selection candidates, a second selection function for comparing the periods of the respective terms of the polynomials decided by the nonlinear least squares method, with the initial values of the periods set from the inverse numbers of the peak frequencies of power spectral densities, to reject the generalized trigonometric polynomial expressions, for which the differences obtained as results of the comparison are not lower than a set value, and to retain the other generalized trigonometric polynomial expressions as selection candidates, and a third selection function for comparing the powers obtained from the amplitudes of the respective terms of the polynomials decided by the nonlinear least squares method, with the powers of the peaks corresponding to power spectral densities pair by pair, to reject the generalized trigonometric polynomial expressions having the amplitudes, the differences of which obtained as results of the comparison are not lower than a set value, and to retain the other generalized trigonometric polynomial expressions as selection candidates, wherein the processings by the first, second and third selection functions are performed one after another for selecting the generalized trigonometric polynomial expression(s) high in validity and consistency.

Further, this invention proposes the abovementioned time series data analyzer, wherein the third processing means has a fourth selection function for selecting the generalized trigonometric polynomial expression smallest in the standard deviation of residuals in the case where multiple generalized trigonometric polynomial expressions remain as selection candidates after performing the processings by the first, second and third selection functions one after another.

Further, this invention proposes the abovementioned time series data analyzer, wherein the third processing means has a fifth selection function for selecting the longest sample segment as the optimum sample segment in the case where multiple sample segments having the selected generalized trigonometric polynomial expression remain after performing the processings by the first, second and third selection functions to ensure that the sample segment selected by the fifth selection function can be selected as the optimum segment and that the lag value used for calculating the power spectral densities in correspondence to the selected generalized trigonometric polynomial expression can be selected as the optimum lag value for the sample segment.

Further, this invention proposes the abovementioned time series data analyzer, wherein the third processing means has a fifth selection function for selecting the longest sample segment as the optimum sample segment in the case where multiple sample segments having the selected generalized trigonometric polynomial expression remain after performing the processings by the first, second, third and fourth selection functions, to ensure that the sample segment selected by the fifth selection function can be selected as the optimum segment and that the lag value used for calculating the power spectral densities in correspondence to the selected generalized trigonometric polynomial expression can be selected as the optimum lag value for the sample segment.

Further, this invention proposes the abovementioned time series data analyzer, wherein the analysis execution section comprises a segment preparation means for obtaining segments from the time series data on the basis of the optimum segment length derived by the optimum analysis condition deriving section and set in the analysis condition setting means, a power spectral density calculation means for calculating the power spectral densities for the prepared segments by the maximum entropy method using the optimum lag value derived by the optimum analysis condition deriving section and set in the analysis condition setting means, a peak extraction means for extracting the number of dominant peaks of the calculated power spectral densities, and the center frequencies and peak powers of the respective peaks, and a characteristic quantity extraction means for extracting characteristic quantities from the extracted peak string.

Further, this invention proposes the abovementioned time series data analyzer, wherein the analysis condition setting means has a function for setting the optimum analysis conditions derived by the optimum analysis condition deriving section as they are, a function for setting the analysis conditions inputted by an input means, and a selection function thereof.

Further, this invention proposes the abovementioned time series data analyzer, wherein the peak extraction means extracts dominant peaks by a first processing of obtaining a locally prominent peak in each range as wide as several times the average interval between peaks obtained from all the peaks of power spectral densities, and fusing the obtained prominent peak with any adjacent peak within each interval shorter than the average interval, for forming a fused peak, and by a second processing of fusing all the peaks other than the prominent peaks and the fused peaks with the nearest prominent peak or fused peak respectively, wherein in the case where multiple peaks are fused, the peak powers prevailing before and after the fusion areconserved, and the center frequency of each fused peak is obtained in proportion to the peak powers of the multiple peaks existing before the fusion.

Further, this invention proposes the abovementioned time series data analyzer, wherein the characteristic quantity extraction means comprises a trend line calculation means for obtaining the gradient and y-intercept of the trend line of the so-called exponential spectrum by the linear least squares method for a set of the logarithmic peak power values and peak frequencies of the multiple dominant peaks extracted by the peak extraction means, a relative power calculation means for obtaining relative power by dividing the peak power values of all the peaks obtained by the power spectral density calculation means, by the power values shown by the trend line, for normalization, and a characteristic quantity calculation means for calculating characteristic quantities of the relative peak power distribution from the peaks discretely arranged on the frequency axis and the relative peak powers thereof.

Further, this invention proposes the abovementioned time series data analyzer, wherein the time series data is electroencephalogram data, and the characteristic quantities extracted by the characteristic quantity extraction means include three frequencies at which the integrated value obtained by integrating the relative peak powers from the low frequency side in the frequency band of interest of the electroencephalogram spectrum usually ranging from 1 to 30 Hz or 0.5 to 30 Hz corresponds to 25%, 50% or 75% of the total relative peak power of the frequency band of interest.

Further, this invention proposes a computer-readable recording medium recording a time series data analysis program, for analyzing the segments obtained from time series data, comprising a step of inputting the shortest segment length, the longest segment length, and the total number of obtained segments including the shortest segment, the longest segment and the segments with different lengths ranging from the shortest segment length to the longest segment length, or each time step between the shortest segment and the longest segment, as input items, a step of inputting the minimum lag value, the maximum lag value, and the intervals for setting the series of lag values between the minimum lag value and the maximum lag value, as input items, a step of analyzing each of all the segments on the basis of the inputted segment conditions and the inputted analysis conditions, under all the analysis conditions by the maximum entropy method and the nonlinear least squares method, for selecting one appropriate segment and one appropriate analysis condition from all the analysis results and deriving the analysis conditions consisting of the optimum segment length and the optimum lag value in correspondence to the selected results, and a step of setting the derived optimum analysis conditions as analysis conditions for executing the analysis by the maximum entropy method.

Further, this invention proposes the abovementioned computer-readable recording medium recording a time series data analysis program, wherein the step of deriving analysis conditions comprises a step of obtaining multiple segments different in length from the time series data on the basis of the inputted segment conditions and setting them as sample segments, a step of setting analysis conditions, a first processing step of calculating power spectral densities for each of all the set sample segments under all the set analysis conditions using the maximum entropy method, a second processing step of extracting dominant spectral peaks for the respective power spectral densities obtained by the first processing step, and calculating the respective quantities of the generalized trigonometric polynomial expressions for the sample segments from the dominant spectral peaks by the nonlinear least squares method, and a third processing step of determining the validities of the generalized trigonometric polynomial expressions obtained by the second processing step for the sample segment data and the consistencies of the generalized trigonometric polynomial expressions for the power spectral densities, to select one sample segment corresponding to the generalized trigonometric polynomial expression high in validity and consistency, and for deriving the segment length and the lag value corresponding to the selected sample segment, as the optimum segment length and the optimum lag value.

Further, this invention proposes the abovementioned compute-readable recording medium recording a time series data analysis program, wherein the second processing step has a step of extracting the number of the dominant spectral peaks, and the peak frequencies and peak powers of the dominant spectral peaks from the power spectral densities calculated by the first processing step, and a step of calculating the respective quantities of the generalized trigonometric polynomial expressions by calculation of the nonlinear least squares method for minimizing the sum of squares of residuals, with the abovementioned number as the number of terms, and with the inverse numbers of the respective peak frequencies as the initial values of the periods of respective trigonometric terms, and the third processing step has a first selection step of comparing the standard deviations of the residuals in the respective quantities of the generalized trigonometric polynomial expressions concerning the respective sample segments, with a set value, to reject the generalized trigonometric polynomial expressions, the standard deviations of which are not lower than the set value and to retain the other generalized trigonometric polynomial expressions as selection candidates, a second selection step of comparing the periods of the respective terms of the polynomials decided by the nonlinear least squares method, with the initial values of the periods set from the inverse numbers of the peak frequencies of power spectral densities, to reject the generalized trigonometric polynomial expressions, for which the differences obtained as results of the comparison are not lower than a set value, and to retain the other generalized trigonometric polynomial expressions as selection candidates, and a third selection step of comparing the powers obtained from the amplitudes of the respective terms of the polynomials decided by the nonlinear least squares method, with the powers of the peaks corresponding to power spectral densities pair by pair, to reject the generalized trigonometric polynomial expressions having the amplitudes, the differences of which obtained as results of the comparison are not lower than a set value, and to retain the other generalized trigonometric polynomial expressions as selection candidates, wherein the processings by the first, second and third selection steps are performed one after another for selecting the generalized trigonometric polynomial expression(s) high in validity and consistency.

Further, this invention proposes the abovementioned recording medium recording a time series data analysis program, wherein the third processing step has a fourth selection step of selecting the generalized trigonometric polynomial expression smallest in the standard deviation of residuals in the case where multiple generalized trigonometric polynomial expressions remain as selection candidates after performing the processings by the first, second and third selection steps one after another.

Further, this invention proposes the abovementioned recording medium recording a time series data analysis program, wherein the third processing step has a fifth selection step of selecting the longest sample segment as the optimum sample segment in the case where multiple sample segments having the selected generalized trigonometric polynomial expression remain as selection candidates after performing the processings by the first, second and third selection steps, to ensure that the sample segment selected by the fifth selection step can be selected as the optimum segment and that the lag value used for calculating the power spectral densities in correspondence to the selected generalized trigonometric polynomial expression can be selected as the optimum lag value for the sample segment.

Further, this invention proposes the abovementioned recording medium recording a time series data analysis program, wherein the third processing step has a fifth selection step of selecting the longest sample segment as the optimum sample segment in the case where multiple sample segments having the selected generalized trigonometric polynomial expression remain as selection candidates after performing the processings by the first, second, third and fourth selection steps, to ensure that the sample segment selected by the fifth selection step can be selected as the optimum segment and that the lag value used for calculating the power spectral densities in correspondence to the selected generalized trigonometric polynomial expression can be selected as the optimum lag value for the sample segment.

Further, this invention proposes a computer-readable recording medium recording a time series data analysis program, wherein the analysis execution step comprises a segment preparation step of obtaining segments from the time series data on the basis of the optimum segment length derived by the optimum analysis condition deriving step and set in the analysis condition setting means, a power spectral density calculation step of calculating the power spectral densities for the prepared segments by the maximum entropy method using the optimum lag value derived by the optimum analysis condition deriving step and set in the analysis condition setting means, a peak extraction step of extracting the number of dominant peaks of the calculated power spectral densities, and the center frequencies and peak powers of the respective peaks, and a characteristic quantity extraction step of extracting characteristic quantities from the extracted peak string.

Further, this invention proposes the abovementioned computer-readable recording medium recording a time series data analysis program, wherein the analysis condition setting means comprises a function for setting the optimum analysis conditions derived by the optimum analysis condition deriving step as they are, a function for setting the analysis conditions inputted by an input means, and a selection function thereof.

Further, this invention proposes the abovementioned computer-readable recording medium recording a time series data analysis program, wherein the peak extraction step comprises a first processing step comprising a step of obtaining the average interval between peaks from all the peaks of power spectral densities, a step of obtaining a locally prominent peak in each range as wide as several times the obtained average interval and a step of fusing the obtained prominent peak with any adjacent peak within each interval shorter than the average interval for forming a fused peak, and a second processing step of fusing all the peaks other than the prominent peaks and the fused peaks with the nearest prominent peak or fused peak respectively, wherein in the first processing step and the second processing step, in the case where multiple peaks are fused, the peak powers prevailing before and after the fusion are conserved, and the center frequency of each fused peak is obtained in proportion to the peak powers of the multiple peaks existing before the fusion.

Further, this invention proposes the abovementioned recording medium recording a time series data analysis program, wherein the characteristic quantity extraction step comprises a trend line calculation step of obtaining the gradient and y-intercept of the trend line of the so-called exponential spectrum by the linear least squares method for a set of the logarithmic peak power values and peak frequencies of the multiple dominant peaks extracted by the peak extraction step, a relative power calculation step of obtaining relative power by dividing the peak power values of all the peaks obtained by the power spectral density calculation means, by the power values shown by the trend line, for normalization, and a characteristic quantity calculation step of calculating characteristic quantities of the relative peak power distribution from the peaks discretely arranged on the frequency axis and the relative peak powers thereof.

Further, this invention proposes the abovementioned recording medium recording a time series data analysis program, wherein the time series data is electroencephalogram data, and the characteristic quantities extracted by the characteristic quantity extraction step include three frequencies at which the integrated value obtained by integrating the relative peak powers from the low frequency side in the frequency band of interest of the electroencephalogram spectrum usually ranging from 1 to 30 Hz or 0.5 to 30 Hz corresponds to 25%, 50% or 75% of the total relative peak power of the frequency band of interest.

According to the analyzer and the analysis program of this invention, the optimum analysis condition deriving section or the optimum analysis condition deriving step derives a segment length and a lag value that can best provide generalized trigonometric polynomial expressions capable of reproducing the segments of the time series data to be analyzed, and with the segment length and the lag value as the optimum segment length and the optimum lag value, the analysis execution section or the analysis execution step performs analysis by the maximum entropy method. Therefore, the segments of the time series to be analyzed are expected to be outputs respectively from a system in a certain dynamic state over the entire length, and the behavior of time series data such as electroencephalogram data on the time base is expected to be consistent with the behavior of MED-PSDs on the frequency axis.

Therefore, as a result of the consistency assured as described above, the respective quantities characterizing the time series data such as the gradient and divisional powers of the spectrum obtained in the analysis execution section or the analysis execution step can be more reliable compared with the quantities obtained by the conventional method.

Further, according to the analyzer and the analysis program of this invention, in addition to the respective quantities obtained by the conventional electroencephalogram analysis, the fundamental features of the spectrum are described in more detail not only by the gradient of the trend line but also by a set of the frequencies at which the integrated value of the relative peak powers (the intensities of respective peak powers relative to the trend line) in the frequency band of interest corresponds to ¼, ½ or ¾ of the total sum in the frequency band of interest. Therefore, the findings concerning the dynamic state of a system (brain) that can not be obtained by the conventional method can be obtained.

DESCRIPTION OF THE INVENTION

Embodiments of the time series data analyzer of the present invention are described below in reference to the attached drawings.

Figure 1:
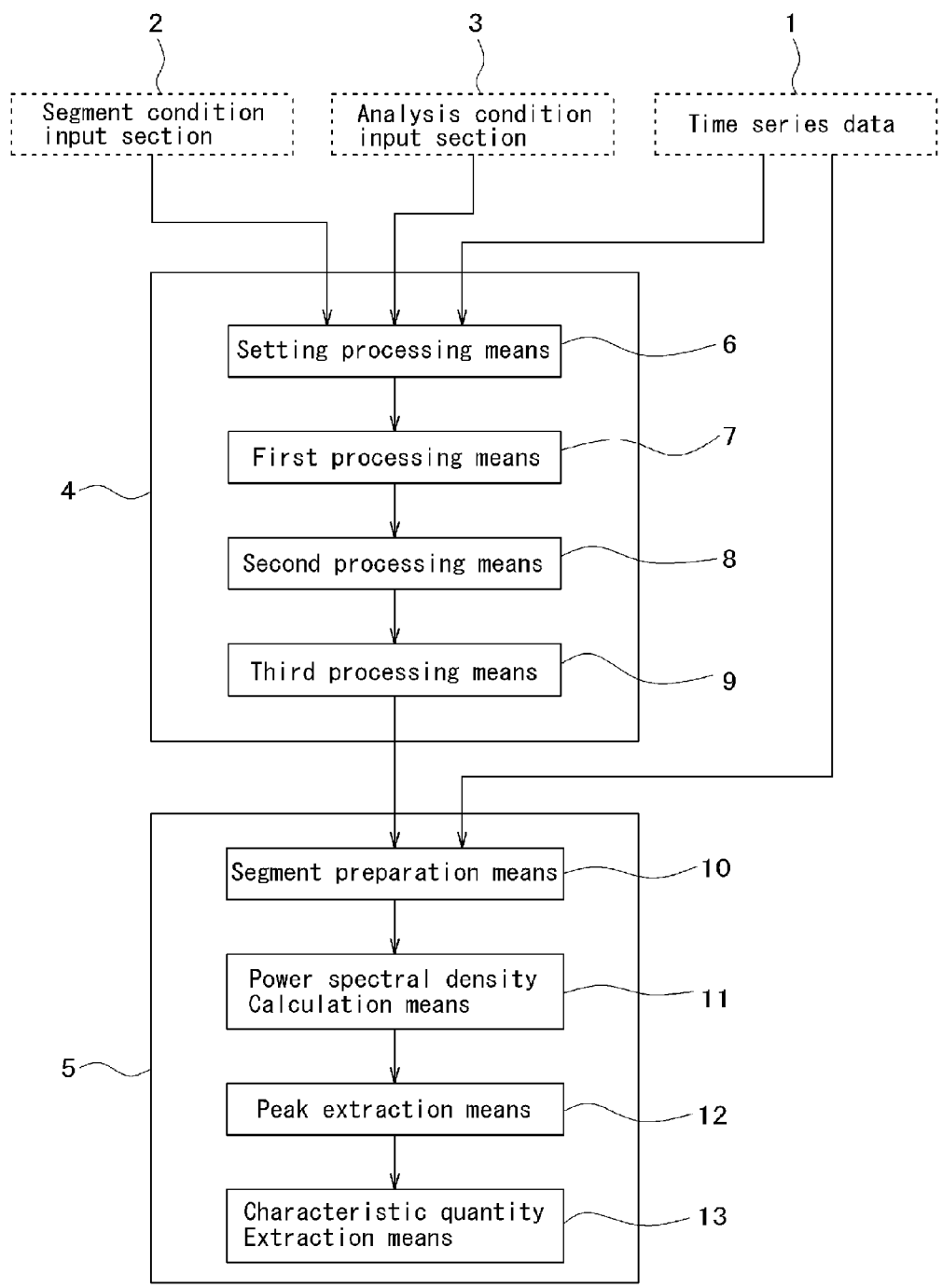
FIG. 1 is a diagram for explaining the entire constitution typically expressing an embodiment of the analyzer of this invention.

At first, FIG. 1 is a diagram typically showing the entire constitution of the analyzer of this invention. The analyzer for analyzing the segments obtained from time series data 1 comprises a segment condition input section 2 into which the shortest segment length, the longest segment length, and the total number of obtained segments including the shortest segment, the longest segment and the segments with different lengths ranging from the shortest segment length to the longest segment length, or each time step between the shortest segment and the longest segment are inputted as input items, an analysis condition input section 3 into which the minimum lag value, the maximum lag value, and the intervals for setting the series of lag values between the minimum lag value and the maximum lag value are inputted as input items, an optimum analysis condition deriving section 4 in which each of all the segments is analyzed on the basis of the segment conditions inputted in the segment condition input section 2 and the analysis conditions inputted in the analysis condition input section 3, under all the analysis conditions by the maximum entropy method and the nonlinear least squares method, for selecting one appropriate segment and one appropriate analysis condition from all the analysis results and deriving the optimum segment length and the optimum lag value in correspondence to the selected results, and an analysis execution section 5 in which analysis is executed by the maximum entropy method on the basis of the optimum analysis conditions derived by the optimum analysis condition deriving section 4.

Further, in this embodiment, the optimum analysis condition deriving section 4 comprises a setting processing means 6 for obtaining multiple segments different in length from the time series data 1 on the basis of the conditions inputted in the segment condition input section 2, to set the segments as sample segments and for reading the analysis conditions inputted in the analysis condition input section 3, to set the analysis conditions, a first processing means 7 for calculating the power spectral densities for each of all the sample segments set by the setting processing means 6, under all analysis conditions using the maximum entropy method, a second processing means 8 for extracting the dominant spectral peaks for the respective power spectral densities obtained by the first processing means 7, and calculating the respective quantities of the generalized trigonometric polynomial expressions about the sample segments from the dominant spectral peaks by the nonlinear least squares method, and a third processing means 9 for determining the validities of the generalized trigonometric polynomial expressions obtained by the second processing means 8 for the sample segment data and the consistencies of the generalized trigonometric polynomial expressions for the power spectral densities, to select one sample segment corresponding to the generalized trigonometric polynomial expression high in validity and consistency, for deriving the segment length and the lag value corresponding to the sample segment as the optimum segment length and the optimum lag value.

Furthermore, in this embodiment, the analysis execution section 5 comprises a segment preparation means 10 for obtaining segments from the time series data 1 on the basis of the optimum segment length derived by the optimum analysis condition deriving section 4, a power spectral density calculation means 11 for calculating the power spectral densities for the prepared segments by the maximum entropy method using the optimum lag value derived by the optimum analysis condition deriving section 4, a peak extraction means 12 for extracting the number of dominant peaks of the calculated power spectral densities, and the center frequencies and peak powers of the respective peaks, and a characteristic quantity extraction means 13 for extracting characteristic quantities from the extracted peak string.

The analysis execution section 5 comprises an analysis condition setting means though not shown in the drawings, and the analysis condition setting means comprises a function for setting the optimum analysis conditions derived by the optimum analysis condition deriving section 4 as they are, a function for setting the analysis conditions inputted by an input means (not shown in the drawings), and a selection function thereof.

The operation of the time series data analyzer of this invention with the above constitution is explained below with electroencephalogram data as the time series data to be analyzed.

At first, the overall trend of a spectrum means the "gradient" of the trend line of the frequency distribution of the powers constituting a time series. In the case of the above-mentioned exponential spectrum, if the spectrum is plotted as a semilogarithmic graph, the trend line is a straight line, and the gradient of the straight line is the overall trend of the spectrum.

Figure 4:
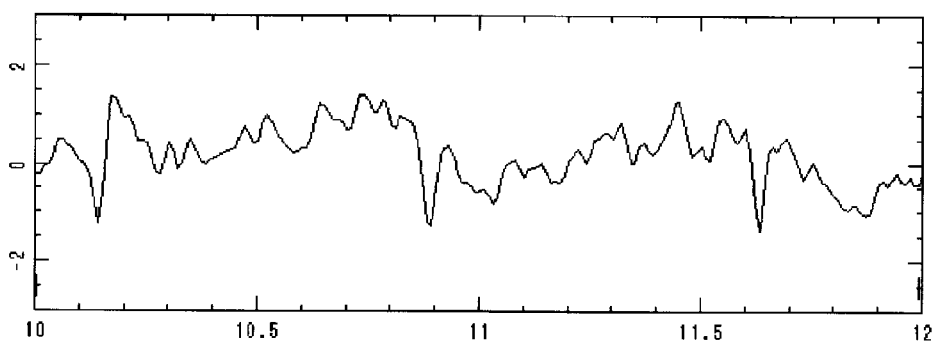
FIG. 4 is diagrams showing an electroencephalogram and the spectrum thereof as an example.
Figure 4:
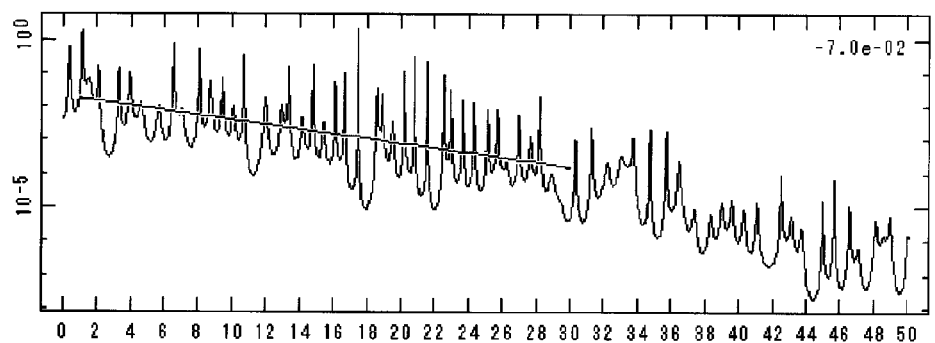

FIG. 4 shows electroencephalogram data of 2 seconds and the spectral densities thereof as an example. FIGS. 4(*a*) shows electroencephalogram data, and (*b*), spectral densities. As can be seen from the diagrams, the electroencephalogram greatly varies in a very short period of 2 seconds, and the spectrum thereof comprises numerous peaks. The peaks attenuate exponentially in the frequency band of interest (1 to 30 Hz or 0.5 to 30 Hz). Meanwhile, this diagram shows the result of analyzing the data of 2 seconds obtained as a segment from large electroencephalogram data presented as time series data.

How to decide the length of data to be analyzed as a segment has not been clearly considered. The data length (the number of data points) has been decided exclusively for the convenience of analysis. That is, since FFT is mainly used for calculation of spectra, the data to be analyzed is decided to have the number of data points equal to any power of 2 suitable for the analysis.

Figure 5:
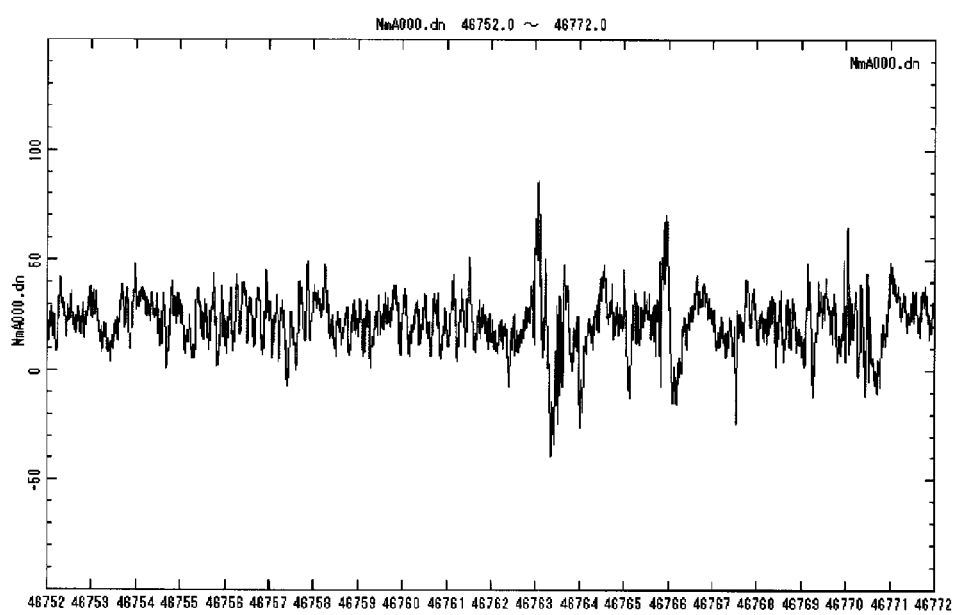
FIG. 5 is a diagram showing electroencephalogram data of 20 seconds evidently different in state between the former half and the latter half.

On the other hand, in the first place, to obtain the overall trend of the spectrum of time series data is to obtain the most basic and fundamental indicator concerning the dynamic state of the system generating the time series data, and it should be assumed that the dynamic state of the system remains certain over the segment length (time) of the time series data to be analyzed as a package. For example, in an extreme case, even if the data of a segment containing the data immediately before an attack of epilepsy and the data immediately after the attack is analyzed as a package, the overall trend of the spectrum as an analysis result cannot have any primary meaning. FIG. 5 shows an example of electroencephalogram data in such a case, and it can be seen that the state of the former half in the data with a length of 20 seconds is evidently different from that of the latter half.

If it is intended to effectively use the overall trend of the spectrum of time series data, the time series data to be analyzed, in this case, electroencephalogram data is required to remain in the same dynamic state in the segment, the spectrum of which is going to be obtained. The analyzer of this invention can obtain the optimum analysis conditions including the optimum segment length considered to be in a certain dynamic state by the following operation, to thereby perform optimum analysis.

Figure 2:
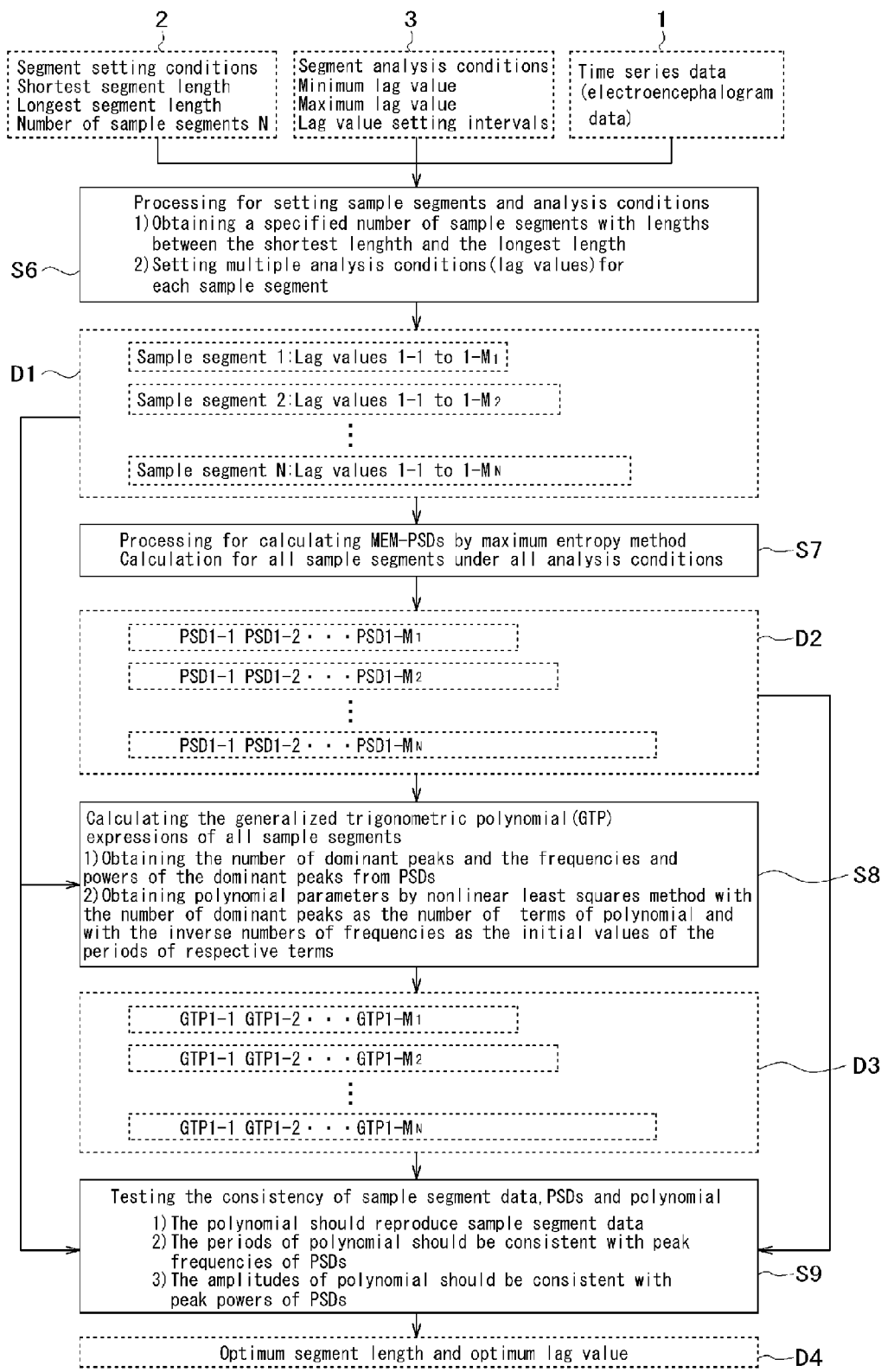
FIG. 2 is a diagram for typically showing a partial constitution of the analyzer of this invention and the flow of the processing by the analyzer.

At first, in FIG. 2 that shows the operation of the optimum analysis condition deriving section 4, not only the shortest length and the longest length of the segments to be examined as to whether or not each of them remains in the same dynamic state, but also the total number of obtained segments including the shortest segment, the longest segment and the segments with different lengths ranging from the shortest segment length to the longest segment length or each time step between the shortest segment and the longest segment are inputted into the segment condition input section 2 beforehand.

In the analysis of an electroencephalogram, the frequency band of interest ranges from 1 to 30 Hz or from 0.5 to 30 Hz. Therefore, as the shortest segment length, the length on the order of the inverse number of the lower limit frequency, for example, a length of 2 seconds is inputted. Further, in general, in the case where an electroencephalogram is visually determined, determination is made every 30 seconds, but the electroencephalogram varies variously, and does not show the same state over the entire time length of 30 seconds. Therefore, as the longest segment length, a fraction of 30 seconds, for example, a length of 5 seconds is inputted. Further, the total number N of the segments to be obtained in a set length of 2 to 5 seconds is seven if, for example, examination is made in time steps of 0.5 second. Therefore, either the total number N of segments or each time step can be inputted into the segment condition input section 2.

Next, the analysis conditions, i.e., the lag values to be used for analyzing the multiple sample segments set according to the segment conditions inputted in the segment condition input section 2, by the maximum entropy method in the analysis execution section 5 are inputted into the analysis condition input section 3 beforehand.

The lag values as analysis conditions can be inputted by obtaining the range of the lag values, etc. from the findings obtained from the results of analyzing many sets of time series data by the maximum entropy method. For example, in the case of electroencephalogram data, if the lag value is assumed to be changed in the range from 50 to 75% of the data length, 0.5 is inputted as the minimum lag value (rate to the number of segment data points) while 0.75 is inputted as the maximum lag value. Further, if the lag value is calculated every step of 5%, 0.05 is inputted as the lag value setting intervals.

Meanwhile, the time series data 1 in FIG. 2 is the whole or a part of observed electroencephalogram data, and is required to be at least longer than the abovementioned longest segment length.

Next, at first at the step S6 corresponding to the aforementioned setting processing means 6, the optimum analysis condition deriving section 4 obtains multiple segments different in length from the time series data 1 on the basis of the conditions inputted in the segment condition input section 2, to set them as sample segments and reads the analysis conditions, i.e., the lag values inputted in the analysis condition input section 3, to set them.

Symbol D1 shows the contents set in the setting processing means 6. N sample segments (1 to N) in total obtained from the time series data 1 and multiple lag values for the respective sample segments (1-1 to 1-M$_1$, 1-1 to 1-M$_2$, . . . , 1.1 to 1-M$_N$) are set.

In this case, sample segments are obtained from the time series data and set in such a manner that long segments may include short segments. In this case, the sample segments respectively different in length can be obtained in such a manner that they may fit each other at any of the initial point, central point or final point.

Next, at the step S7 corresponding to the first processing means 7, the optimum analysis condition deriving section 4 performs the calculation processing of MEM-PSDs for the respective sample segments (1 to N) of D1 by the maximum entropy method using the set multiple lag values (1-1 to 1-$M_1$, 1-1 to 1-$M_2$, . . . , 1-1 to 1-$M_N$) according to the following formula.

$$B_m(f) = \frac{\Delta t P_m}{\left|1 + \sum_{k=1}^{m} \gamma_m(k)e^{-i2\pi fk\Delta t}\right|^2} \quad \text{Equation 1}$$

where $B_m(f)$ is the spectral density at frequency f calculated using lag value m; $\Delta t$ is a sampling interval; and $P_m$ and $\gamma_m(k)$ are Berg coefficients of degree m.

As indicated, for example, in Document 4, the maximum entropy method (MEM) can analyze a given number of data points, and therefore unlike the analysis by FFT, the setting of sample segments is not restricted by the sampling frequency or the number of data points of time series data, i.e., electroencephalogram data in this case.

Document 4

Kazuo TOKIWANO, Norio OHTOMO and Yukio TANAKA, "Time Series Data Analysis by the Maximum Entropy Method—Theory and Practice of MemCalc—(in Japanese)," First Edition, Book Publishing Committee, Hokkaido University, Jun. 25, 2002

Thus, by the processing at step S7, multiple power spectral densities (PSD1-1, PSD1-2, . . . , PSD1-$M_1$); (PSD1-1, PSD1.2, . . . , PSD1-$M_2$); . . . ; (PSD1.1, PSD1.2, . . . , PSD1-$M_N$) can be obtained as indicated by symbol D2.

Then, at the step S8 corresponding to the second processing means 8, the optimum analysis condition deriving section 4 extracts dominant spectral peaks for the respective power spectral densities D2 obtained at the step S7, and calculates the respective quantities of generalized trigonometric polynomial expressions represented by the following formula for the sample segments from the dominant spectral peaks by the nonlinear least squares method.

$$x(t) = a_0 + \sum_{j=1}^{M} a_j \cos\frac{2\pi}{T_j}(t - \phi_j) + \varepsilon(t) \quad \text{Equation 2}$$

where x(t) is sample segment data (observed value) at time t; $a_0$ is the level value; M is the number of terms; $a_j$ is the amplitude of j-th trigonometric term; $T_j$ is the period; $\phi_j$ is the acrophase; and $\varepsilon(t)$ is the residual (least squares application error).

The calculation for obtaining a generalized trigonometric polynomial expression is described in the abovementioned document, etc., but is performed according to the following procedure.

(1) At first, the number of dominant spectral peaks, and the respective peak frequencies and respective peak powers of the dominant spectral peaks are taken out of MEM-PSDs.

(2) The number of terms M of the generalized trigonometric polynomial is made to be equal to the number of the dominant spectral peaks, and the initial values of the periods $T_j$ of respective trigonometric terms are set at the inverse numbers of the peak frequencies of the corresponding peaks. Starting from the initial values, sample segment data can be described as a generalized trigonometric polynomial by the nonlinear least squares method (nonlinear LSF) for minimizing the sum of squares of $\varepsilon(t)$, to obtain the respective quantities $a_0$, $a_j$, $T_j$ and $\phi_j$ (j=1 to M) of the generalized trigonometric polynomial expression.

According to the abovementioned procedure, multiple MEM-PSDs can be calculated for the respective sample segments, and thus multiple generalized trigonometric polynomial expressions for the respective sample segments can be obtained. Symbol D3 of FIG. 2 shows multiple generalized polynomial expressions (GTP1-1, GTP1-2, . . . , GTP1-$M_1$); (GTP1-1, GTP1-2, . . . , GTP1-$M_2$); . . . ; (GTP1-1, GTP1-2, . . . , GTP1-$M_N$) obtained for the N sample segments.

Subsequently, at the step S9 corresponding to the third processing means 9, the optimum analysis condition deriving section 4 determines the validities of the multiple generalized trigonometric polynomial expressions D3 obtained at the step S8 for the sample segment data and the consistencies of the generalized trigonometric polynomial expressions for the power spectral densities, to select the generalized trigonometric polynomial expression(s) high in validity and consistency.

The step S9 corresponding to the third processing means 9 has a first selection step of comparing the standard deviations of the residuals in the respective quantities of the generalized trigonometric polynomial expressions for the respective sample segments, with a set value, to reject the generalized trigonometric polynomial expressions, the standard deviations of which are not lower than the set value and to retain the other generalized trigonometric polynomial expressions as selection candidates, a second selection step of comparing the periods of the respective terms of the polynomials decided by the nonlinear least squares method with the initial values of the periods set from the inverse numbers of the peak frequencies of power spectral densities, to reject the generalized trigonometric polynomial expressions, for which the differences obtained as results of the comparison are not lower than a set value, and to retain the other trigonometric polynomial expressions as selection candidates, and a third selection step of comparing the powers obtained from the amplitudes of the respective terms of the polynomials decided by the nonlinear least squares method with the powers of the peaks corresponding to power spectral densities pair by pair, to reject the generalized trigonometric polynomial expressions having the amplitudes, the differences of which obtained as results of the comparison are not lower than a set value, and to retain the other generalized trigonometric polynomial expressions as selection candidates, wherein the processings by the first, second and third selection steps are performed one after another, to select the generalized trigonometric polynomial expression(s) high in validity and consistency.

Further, the step S9 corresponding to the third processing means 9 can comprise a fourth selection step, to select the generalized trigonometric polynomial expression smallest in the standard deviation of residuals, in the case where multiple generalized trigonometric polynomial expressions remain as selection candidates after performing the processings by the first, second and third selection steps one after another.

Further, the step S9 corresponding to the third processing means 9 can comprise a fifth selection step of selecting the longest sample segment as the optimum sample segment in the case where multiple generalized trigonometric polynomial expressions remain as selection candidates after performing the processings by the first, second and third selection steps or by the first, second, third and fourth selection steps, to ensure that the sample segment selected by the fifth selection step can be selected as the optimum segment and that the lag value used for calculating the power spectral densities in correspondence to the selected generalized trigonometric polynomial expression can be selected as the optimum lag value for the sample segment. Thus, analysis conditions D4 consisting of the optimum segment length and the optimum lag value can be derived.

In the above processing, the longest segment length is set at 5 seconds, but the segment length is a practical length for electroencephalogram data, and the segment conditions and analysis conditions including the longest segment length can be set as appropriate in response to time series data. If the length of a sample segment considered to be in a certain dynamic state is longer, it can be expected that the values obtained as analysis results become more stable, and this selection is performed by the abovementioned fifth selection step.

Figure 6:
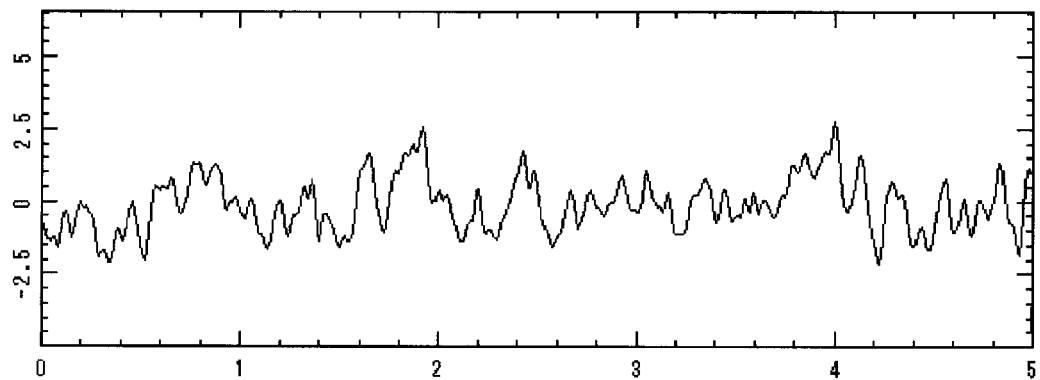
FIG. 6 is diagrams showing electroencephalogram data with a length of 5 seconds, the generalized trigonometric polynomial expression thereof and the residuals thereof.
Figure 6:
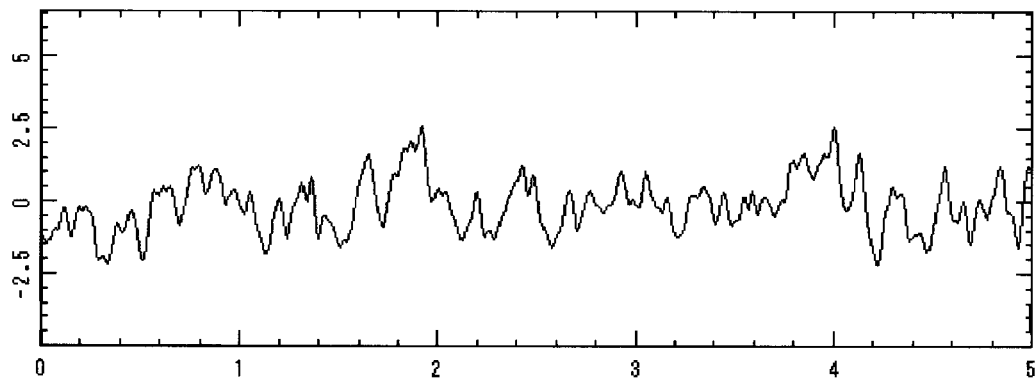
Figure 6:
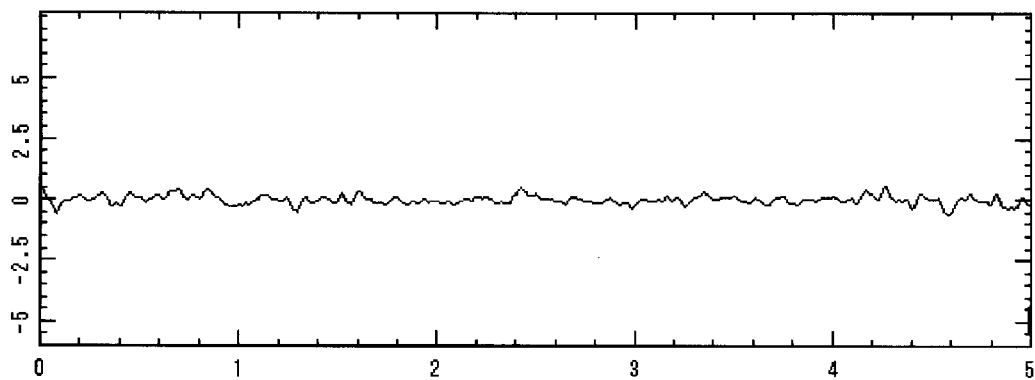

FIG. 6 shows an example in which electroencephalogram data with a length of 5 seconds is expressed by a generalized trigonometric polynomial as a result of the abovementioned processing. FIGS. 6(a) shows electroencephalogram data; (b), a generalized trigonometric polynomial expression; and (c), residuals that cannot be expressed as the sum of trigonometric terms.

As shown in these diagrams, the generalized trigonometric polynomial expression (b) well reproduces the corresponding electroencephalogram data, and the residuals of (c) are small and are distributed near the value zero, without depending on time. It can be seen that the power spectral densities (MEM-PSDs) for giving the initial values of the nonlinear least squares method can be thus precisely calculated by the processing of this invention.

In this invention, as described above, the optimum analysis condition deriving section 4 derives the segment length and the lag value that can provide generalized trigonometric polynomial expressions capable of best reproducing a portion of time series data. Therefore, it can be expected that the segments of the time series data subsequently analyzed by the analysis execution section are outputs respectively from a certain system (brain in this case) in a certain dynamic state over the entire length. The reason is that at the step S9 corresponding to the third processing means 9 of the optimum analysis condition deriving section 4, the validities for the sample segment data and the consistencies for the power spectral densities are determined, to select a generalized trigonometric polynomial expression high in validity and consistency and therefore that all the trigonometric terms of the generalized trigonometric polynomial exist with certain amplitudes over the entire segment data length.

This matter is explained below more particularly in reference to the following example.

At first, in the case where a mode (trigonometric term) with a certain period T and a certain amplitude a exists in the entire region of a segment, the power of the mode is $a^2/2$, and further the power of the spectral peak corresponding to the MEM-PSD is also expected to be $a^2/2$. On the other hand, if the mode exists in the former half only of the segment data, the power of the spectral peak is expected to be halved to $a^2/4$. Furthermore, the amplitude of this mode has at least a value different from a, though the behavior of the amplitude cannot be accurately predicted in view of the relation with the other modes, and the possibility that it happens to agree with the value expected from the peak power is very small. Therefore, if whether or not the peak powers of MEM-PSDs correspond well to the amplitudes of respective modes is determined, whether or not the electroencephalogram data can be regarded to be outputs respectively from a system (brain) with the same dynamic state can be generally decided.

Figure 7:
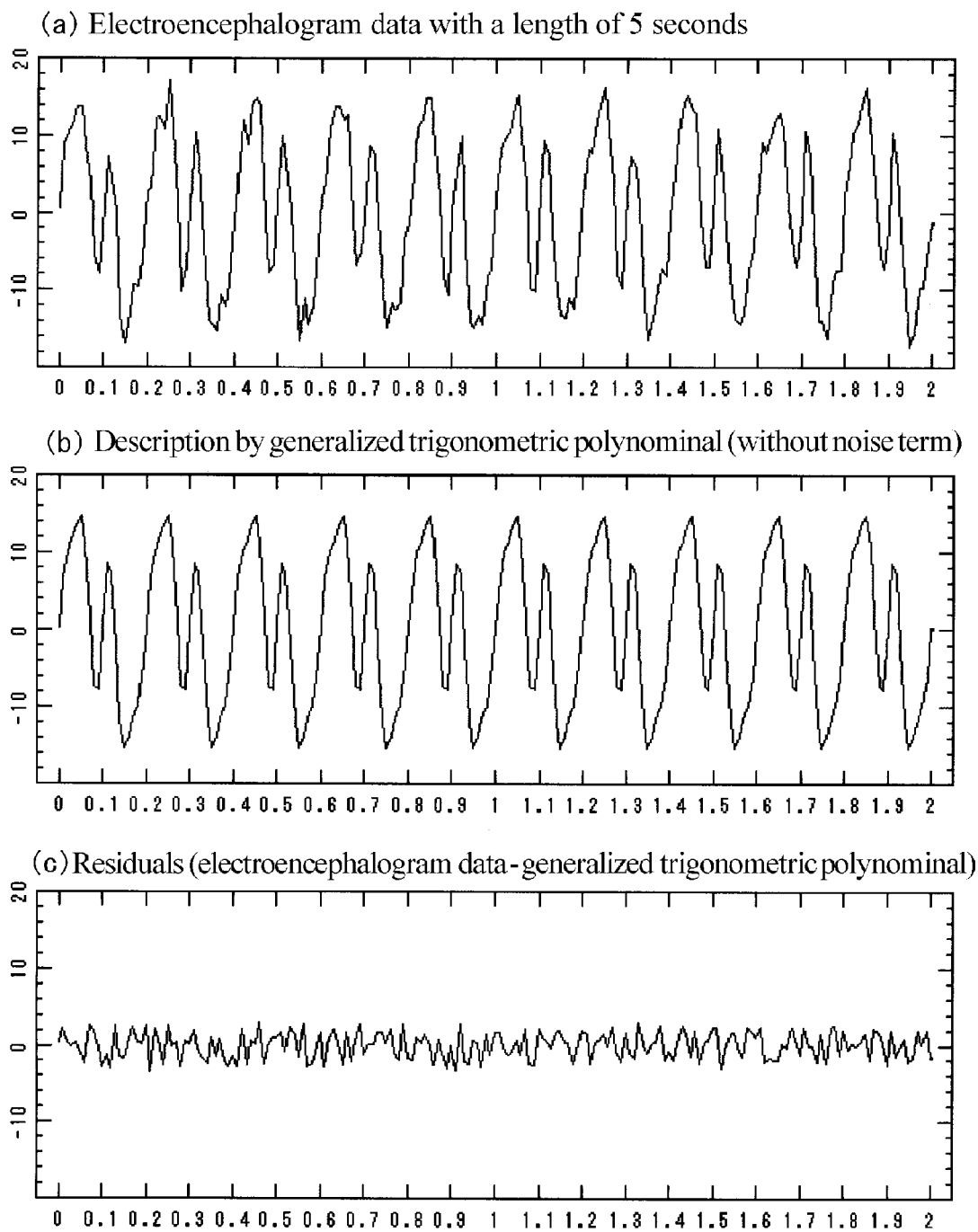
FIG. 7 is diagrams showing artificial time series data and the results of analysis by this invention.
Figure 8:
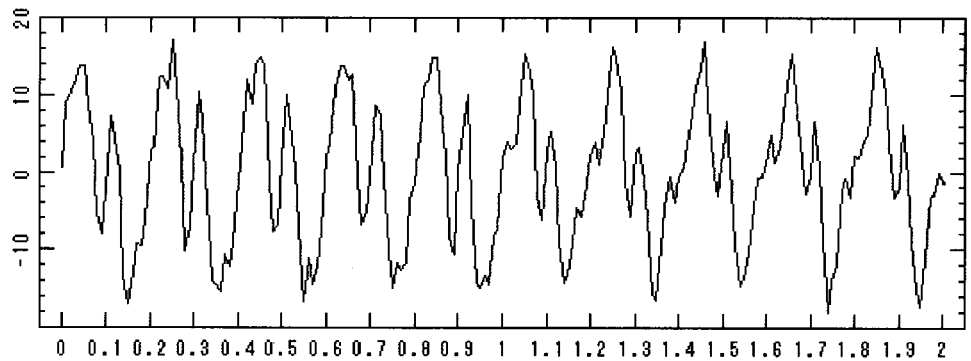
FIG. 8 is diagrams showing artificial time series data partially lacking in mode in the latter half of the data of FIG. 7 and the results of analysis by this invention.
Figure 8:
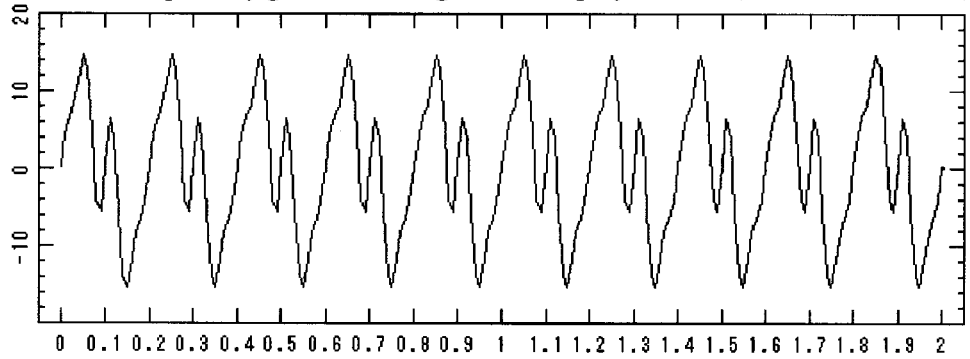
Figure 8:
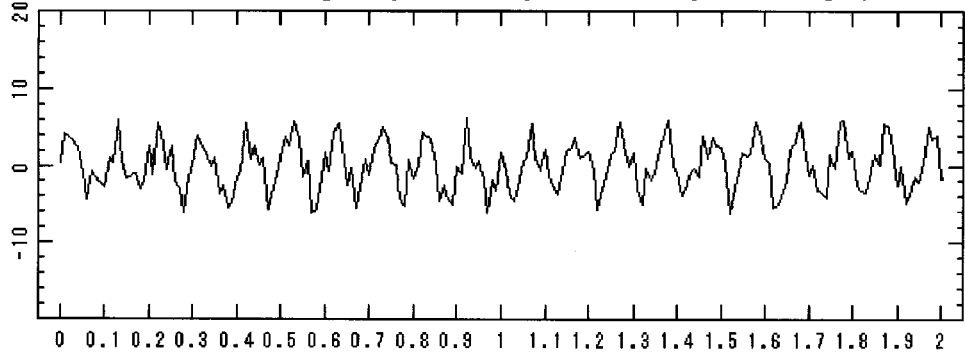

FIGS. 7 and 8 show examples in which respectively artificial time series data with a length of 2 seconds and with 201 points is expressed by a generalized trigonometric polynomial after performing the above processing. Each (a) shows time series data; (b), a generalized trigonometric polynomial expression; and (c), residuals that cannot be expressed by the sum of trigonometric terms.

The time series data of FIG. 7 is data obtained by convoluting noise into four trigonometric terms at 5, 10, 15 and 20 Hz, and the amplitudes of the respective modes are 10, 7, 5 and 3 over the entire length. On the other hand, the time series data of FIG. 8 corresponds to the data obtained by removing the mode of 10 Hz from the data of FIG. 7 for one second only in the latter half.

In the comparison between FIGS. 7 and 8, in the case of FIG. 7, as in the case of FIG. 6, the generalized trigonometric polynomial expression of (b) well reproduces the time series data of (a), and the residuals of (c) are small and are distributed near the value zero, without depending on time. On the contrary, in the case of the time series data shown in (a) of FIG. 8 lacking in the mode of 10 Hz in the latter half of the region, the application of the modes does not fit well as shown in (b), and large residuals remain as shown in (c).

FIGS. 9(a) and (b) relate to the time series data of FIGS. 7 and 8 respectively and show the parameters of four trigonometric terms as the results of processing at the step S9 corresponding to the third processing means 9 of the optimum analysis condition deriving section 4.

As can be seen from the drawing, in the case where the mode of 10 Hz is missing in the latter half, the amplitude shows a small value of 3.62 (power 6.55) compared with the amplitude 7.0 (power 24.5) of the original mode. Meanwhile, the peak power of the MEM-PSD at 10 Hz can be calculated as 26.5 in the case of the time series data of FIG. 7 without lacking, but as 12.9 in the case of the time series data of FIG. 8 with lacking.

As described above, in this invention, it can be expected that the segments of the time series data to be analyzed by the analysis execution section are outputs respectively from a system in a certain dynamic state over the entire length. In other words, this invention provides a method for determining the dynamic stability of electroencephalogram data over the segment length on the basis of the consistency between the amplitudes of the respective terms of a generalized trigonometric polynomial and the peak powers of MEM-PSDs.

Next, the operation of the analysis execution section 6 is explained below in reference to FIG. 3.

At first, at the step S10 corresponding to the segment preparation means 10, each segment data D5 to be analyzed is obtained from the time series data 1, i.e., large electroencephalogram data on the basis of the optimum segment length among the optimum analysis conditions D4 derived by the optimum analysis condition deriving section 4. As described above, the obtained segment data D5 is expected to be an output from a system in a certain dynamic state over the entire length.

Then, at the step S11 corresponding to the power spectral density calculation means 11, power spectral densities (MEM-PSDs) D6 are calculated by the maximum entropy method for the obtained segment D5 on the basis of the optimum lag value in the optimum analysis conditions D4 derived by the optimum analysis condition deriving section 4.

Meanwhile, as the segment length of the time series data analyzed in the analysis execution section 5 and the analysis conditions thereof, the optimum analysis conditions D4 derived by the optimum analysis condition deriving section 4 can be used as described above. Otherwise, in the case where sufficient findings are already accumulated for the operations of the optimum analysis condition deriving section 4 for the time series data concerned or similar time series data, those values can also be directly specified.

Then, at the step S12 corresponding to the peak extraction means 12, the analysis execution section 5 extracts respective quantities D7 characterizing the power spectral densities, i.e., the number of dominant peaks of the power spectral densities, and the center frequencies and peak powers of the respective peaks.

Subsequently, at the step S13a, S13b and S13c corresponding to the characteristic quantity extraction means 13, characteristic quantities are extracted.

At first, at the step S13a corresponding to the trend line calculation means, the gradient and y-intercept D8 of the trend line of the so-called exponential spectrum are obtained by the linear least squares method for a set of the logarithmic peak power values and peak frequencies of the multiple dominant peaks extracted at the step S12 corresponding to the peak extraction means 12.

Then at the step S13b corresponding to the relative power calculation means, a series of relative power D9 are obtained by dividing the peak power values of all the peaks obtained at the step S11 corresponding to the power spectral density calculation means 11 by the power values shown by the trend line, for normalization.

Further, at the step S13c corresponding to the characteristic quantity calculation means, the characteristic quantities D10 of the relative peak power distribution are obtained from the peaks discretely arranged on the frequency axis and the relative peak powers thereof, and at the subsequent step S13d, the characteristic quantities D11 are outputted.

It should be noted in the above processing steps that the calculation at the step S11 corresponding to the power spectral density calculation means 11 is performed under the optimum analysis conditions D4 derived by the optimum analysis condition deriving section 4 or by directly specifying the values considered as optimum values thanks to the sufficient findings accumulated. Therefore, the series of the dominant peaks of the spectrum as the result of calculation can be regarded to be the respective terms of the generalized trigonometric polynomial expression describing the segment data. In other words, this invention provides a procedure for regarding the dominant peak string of the MEM-PSDs calculated using the optimum segment length and the optimum lag value obtained by the optimum analysis condition deriving section 4, as the respective terms of the generalized trigonometric polynomial describing the segment data.

That is, at the step S13a corresponding to the abovementioned trend line calculation means, the trend line of the series of dominant peaks (the center frequencies and peak powers) is calculated. That is, the trend line of the distribution of the discrete powers formed by the respective terms of a generalized trigonometric polynomial is calculated, and the trend line of the power spectral densities continuously distributed in the entire frequency band is not calculated. Thus, as the result of the processing at the step S13, the trend line, gradient and y-intercept of symbol D8 can be obtained, and the value of the gradient corresponds to the value of the overall trend of the electroencephalogram spectrum obtained by the conventional method.

In this case, in the processing at the abovementioned step S13c, as described later, the relative peak powers contained in the frequency band of interest (1 to 30 Hz or 0.5 to 30 Hz) are integrated from the low frequency side, and three frequencies at which the integrated value corresponds to 25%, 50% or 75% of the total relative peak power in the frequency band of interest can be extracted, to obtain the result D10. The processing at the step S13c is equivalent to the five number summary without minimum and maximum. The characteristic quantities are proposed for the first time in the analyzer of this invention, and the series of results D11 containing them is outputted by the output processing at the step S13d.

Figure 3:
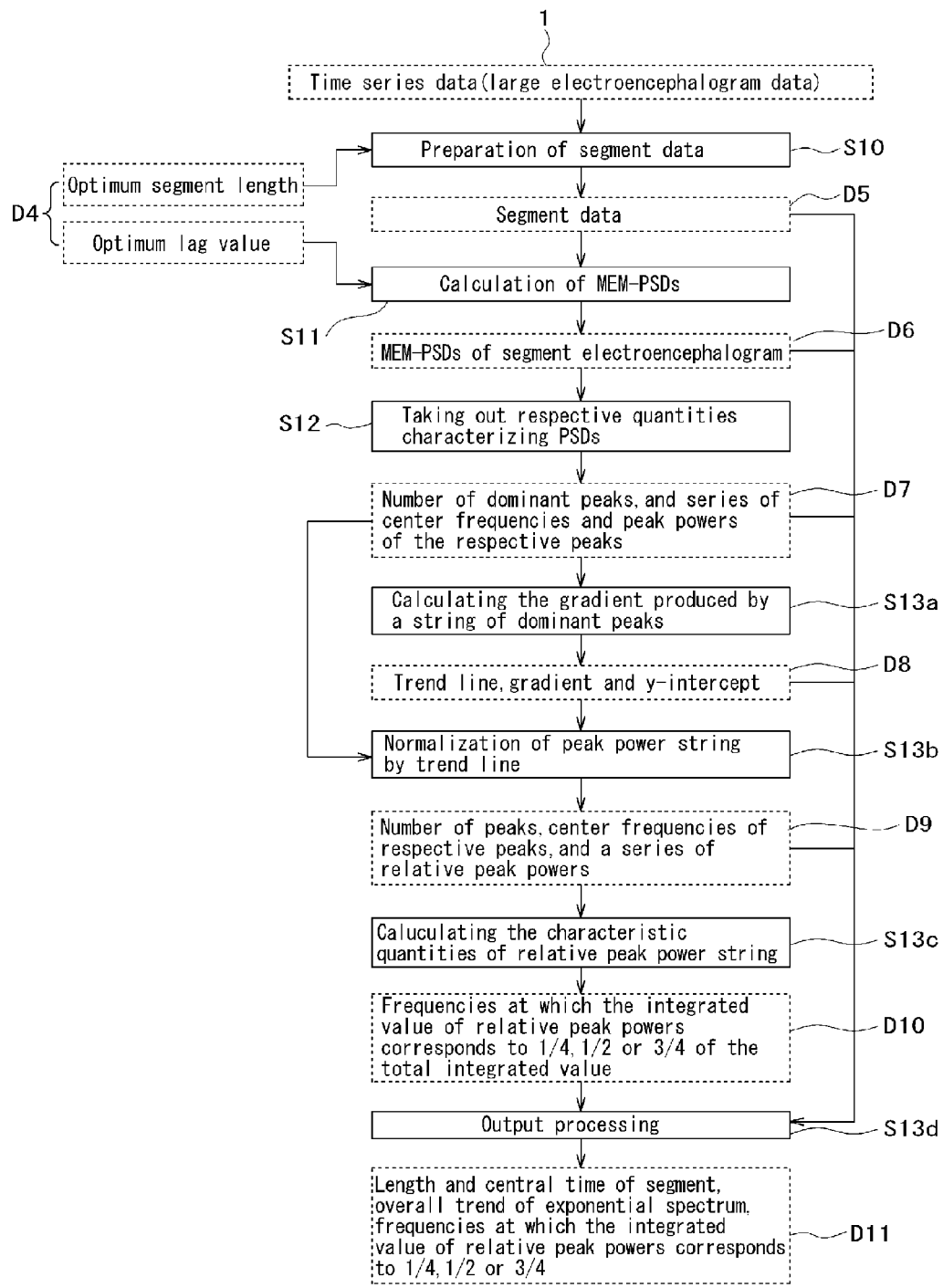
FIG. 3 is a diagram for typically showing another partial constitution of the analyzer of this invention and the flow of the processing by the analyzer.

In addition, though not stated in FIG. 3, in this invention, highly precise MEM-PSDs can be obtained. Therefore, all the characteristic quantities of the conventional method concerning the electroencephalogram spectrum can be calculated. Particularly, they include divisional powers (in $\mu V^2$) at respective frequencies $\delta$, $\theta$, $\alpha$ and $\beta$ (1 to 4 Hz, 4 to 8 Hz, 8 to 13 Hz and 13 to 30 Hz), SMF (Spectral Mid Frequency, the frequency at which the integrated value of powers in 1 to 30 Hz corresponds to 50%), $SEF^{90}$ (Spectral Edge Frequency, the frequency at which the same corresponds to 90%), etc. These quantities are important also for determination of electroencephalograms.

In the case where the analysis of one obtained segment by the analysis execution section 5 has been completed as described above, the analysis processing of the next segment is performed as instructed by a superior control means not shown in the drawing. Usually the control means controls in such a manner that the segments analyzed by the analysis execution section 5 one after another may cover the time series data 1 entirely, but depending on the time series data to be analyzed, the processing can also be performed with clearances formed between the segments.

On the other hand, for performing more highly precise analysis, it is desirable that the optimum segment length and the optimum lag value are obtained by the optimum analysis condition deriving means 4 whenever a segment is analyzed, and that the analysis is performed using those optimum data. However, the processing for obtaining the optimum segment length and the optimum lag value requires much CPU power, etc., and further usually the electroencephalogram requires simultaneous measurement using 20 or more channels. Therefore, it is virtually impossible to update the optimum segment length and the optimum lag value for each segment in real time.

Therefore, it is realistic that the superior control means intermittently actuates the optimum analysis condition deriving section 4 to such an extent that the continuous processing of the analysis execution section 5 is not disturbed, and that the derived results are transferred to the analysis execution section 5 as required.

Meanwhile, in the case where segments are obtained from the time series data one after another to perform analysis, various obtaining methods are applicable; for example, (a) segments are obtained without any clearance formed between them, (b) segments partially duplicating each other are obtained, and (c) segments are obtained, for example, in such a manner that the central times of respective segments can be arranged at certain intervals irrespective of whether there is any clearance or partial duplication. However, in this invention, since segment lengths are variable, the method (c) is easy to handle.

Even if clearances are formed between segments as a result of applying the method (c), no practical inconvenience is caused as far as segments with lengths of several seconds are analyzed at intervals of several seconds for addressing system variations on the order of seconds. This is equivalent to the following case. A blood pressure is decided at every beat, and even if all the blood pressures (maximum blood pressures and minimum blood pressures) of about 100,000 beats per day are unknown, an approximate blood pressure of the day can be determined.

Next, with regard to the operation of the analysis execution section 5, the procedure for obtaining the characteristic quantities D10 from MEM-PSDs is explained below in reference to a particular example of applying to electroencephalogram data as described above.

Figures 9, 10:
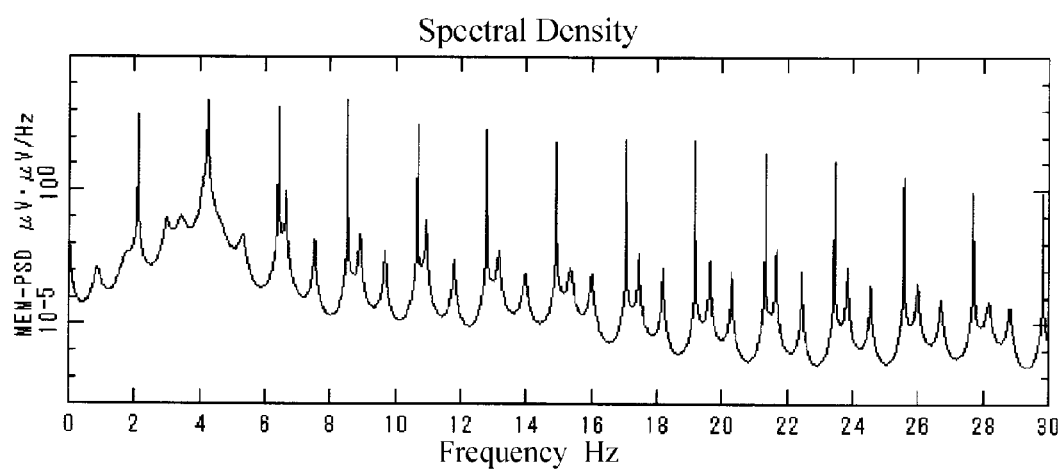
FIG. 9 is illustrations showing the parameters of the trigonometric terms for the respective data types of FIGS. 7 and 8.
FIG. 10 is a diagram showing the MEM-PSDs obtained in the analysis execution section as an example.

At first, FIG. 10 shows an example of MEM-PSDs obtained at the step S11 of the analysis execution section 5.

In FIG. 10, the frequency (Hz) is chosen as the abscissa, and the spectrum density ($\mu V^2/Hz$), as the ordinate. The spectrum is plotted as a semilogarithmic graph for a frequency band of 0 to 30 Hz.

As described above, since the calculation at the step S11 corresponding to the power spectral density calculation means 11 is performed using the optimum analysis conditions D4 derived by the optimum analysis condition deriving section 4 or by directly specifying the values considered to be optimum values on the basis of sufficiently accumulated findings, the MEM-PSDs of FIG. 10 can be expected to have a dynamic structure existing stably over the segment data length obtained from the large electroencephalogram data provided as the time series data 1. That is, the electroencephalogram data x(t) to be analyzed can be described by the following formula as described above.

$$x(t) = a_0 + \sum_{j=1}^{M} a_j \cos\frac{2\pi}{T_j}(t - \phi_j) + \varepsilon(t) \quad \text{Equation 3}$$

and with regard to the dominant peaks of MEM-PSDs, it can be expected that the number of the dominant peaks corresponds to the number of terms M in the above formula, and that (the inverse numbers of) the center frequencies and peak powers of the respective peaks correspond to the periods $T_j$ of the respective terms of the above formula and powers $a_j^2/2$.

Then, by the processing at the step S12, the D7 including the number of the dominant peaks and the series of the center frequencies and powers of the respective peaks is taken out. This processing is performed with a view to deciding the number of terms M and the series of the periods $T_j$ and amplitudes $a_j$ of x(t). In this case, it is necessary that the dynamic structure up to 30 Hz existing in the segment data can be described not too precisely and not too roughly without being partially in the specific frequency band, by the convolution of the M trigonometric terms of the generalized trigonometric polynomial. Meanwhile, the reason why the structure is limited up to 30 Hz is that in the spectral analysis of electroencephalograms, usually the structure from 1 to 30 Hz or 0.5 to 30 Hz is a problem. This can be executed by A. Picking up locally prominent peaks
B. Fusing each prominent peak and any nearby peak into one fused peak
C. Slight peaks are fused with any nearest prominent peak or fused peak.

The sum of the number of prominent peaks and the number of fused peaks is M.

The particular procedure is explained below.

1. Picking Up Peaks

The abovementioned MEM-PSDs have 40 peaks in total (excluding the peak of frequency zero) in the frequency band up to 30 Hz. At first, the center frequencies and peak powers of all the peaks are taken out. Meanwhile, a peak power is the integrated value of the MEM-PSDs in the range from the frequency giving the minimal value immediately before the peak to the similar frequency immediately after the peak. Table 1 shows the series of the peaks obtained as described above.

TABLE 1

Center Frequencies and Peak Powers of All the Peaks of MEM-PSDs

| No. | Frequency(Hz) | Power |
|---|---|---|
| 1 | 0.872 | 0.000289 |
| 2 * | 2.114 | 0.852193 |
| 3 | 3.002 | 0.018925 |
| 4 | 3.449 | 0.031369 |
| 5 * | 4.248 | 24.731433 |
| 6 | 5.315 | 0.004076 |
| 7 * | 6.419 | 1.013633 |
| 8 N | 6.647 | 0.024366 |
| 9 | 7.520 | 0.000651 |
| 10 * | 8.532 | 0.360084 |
| 11 N | 8.914 | 0.001146 |
| 12 | 9.676 | 0.000280 |
| 13 * | 10.671 | 0.132703 |
| 14 N | 10.946 | 0.002369 |
| 15 | 11.795 | 0.000148 |
| 16 * | 12.794 | 0.072841 |
| 17 N | 13.164 | 0.000441 |
| 18 | 13.961 | 0.000084 |
| 19 * | 14.914 | 0.035796 |
| 20 N | 15.347 | 0.000163 |
| 21 | 16.002 | 0.000058 |
| 22 * | 17.055 | 0.020247 |
| 23 N | 17.454 | 0.000149 |
| 24 | 18.186 | 0.000038 |
| 25 * | 19.182 | 0.010827 |
| 26 N | 19.626 | 0.000072 |
| 27 | 20.290 | 0.000025 |
| 28 * | 21.322 | 0.006025 |
| 29 N | 21.657 | 0.000104 |
| 30 | 22.456 | 0.000018 |
| 31 * | 23.446 | 0.003333 |
| 32 N | 23.845 | 0.000039 |
| 33 | 24.553 | 0.000011 |
| 34 * | 25.573 | 0.001856 |
| 35 N | 25.992 | 0.000022 |
| 36 | 26.707 | 0.000007 |
| 37 * | 27.699 | 0.001040 |
| 38 N | 28.163 | 0.000011 |
| 39 | 28.816 | 0.000004 |
| 40 * | 29.827 | 0.000580 |

2. Identifying Locally Prominent Peaks and Nearby Peaks

Then, for the spectral peaks of Table 1, the average peak interval is obtained, and each locally prominent peak is obtained in a range as wide as several times the average interval. The peaks marked with "*" after the corresponding peak number of Table 1 (peak numbers 2, 5, 7, etc.) are the locally prominent peaks found in this way.

Further, if each of the prominent peaks has an adjacent peak existing in a position within the average interval, the peak is identified as a nearby peak. The peaks marked with "N" after the corresponding peak number of Table 1 (peak numbers 8, 11, 14, etc.) are the nearby peaks.

3. Fusing Locally Prominent Peaks with Nearby Peaks

Then, each locally prominent peak is fused with the nearby peak concerned. If there is a nearby peak before or after each prominent peak, they are fused into one fused peak. In this case, the power of the fused peak is the sum of the peak powers of the multiple original peaks. Further, the center frequency of the fused peak is obtained from the center frequencies of the multiple original peaks weighted with the respective peak powers. When the ratio of the power of the prominent peak to the power of the nearby peak is 9:1, the center frequency of the fused peak is the frequency at a position of 1/10 of the frequency interval between the prominent peak and the nearby peak from the center frequency of the prominent peak on the nearby peak side.

Table 2 lists the peaks obtained by removing the nearby peaks as described above.

The number of peaks is decreased from 40 to 29.

TABLE 2

Results of fusing nearby peaks with locally prominent peaks

| No. | Frequency(Hz) | Power |
|---|---|---|
| 1 | 0.872 | 0.000289 |
| 2 * | 2.114 | 0.852193 |
| 3 | 3.002 | 0.018925 |
| 4 | 3.449 | 0.031369 |
| 5 * | 4.248 | 24.731433 |
| 6 | 5.315 | 0.004076 |
| 7 * | 6.424 | 1.037999 |
| 8 | | |
| 9 | 7.520 | 0.000651 |
| 10 * | 8.534 | 0.361230 |
| 11 | | |
| 12 | 9.676 | 0.000280 |
| 13 * | 10.676 | 0.135072 |
| 14 | | |
| 15 | 11.795 | 0.000148 |
| 16 * | 12.796 | 0.073283 |
| 17 | | |
| 18 | 13.961 | 0.000084 |
| 19 * | 14.916 | 0.035959 |
| 20 | | |
| 21 | 16.002 | 0.000058 |
| 22 * | 17.058 | 0.020397 |
| 23 | | |
| 24 | 18.186 | 0.000038 |
| 25 * | 19.185 | 0.010899 |
| 26 | | |
| 27 | 20.290 | 0.000025 |
| 28 * | 21.328 | 0.006130 |
| 29 | | |
| 30 | 22.456 | 0.000018 |
| 31 * | 23.451 | 0.003373 |
| 32 | | |
| 33 | 24.553 | 0.000011 |
| 34 * | 25.578 | 0.001878 |
| 35 | | |
| 36 | 26.707 | 0.000007 |
| 37 * | 27.703 | 0.001051 |
| 38 | | |
| 39 | 28.816 | 0.000004 |
| 40 * | 29.827 | 0.000580 |

4. Fusing Slight Peaks with Prominent Peaks or Fused Peaks

Subsequently all the slight peaks (the peaks other than the prominent peaks and the fused peaks) are fused with the respectively nearest (shortest in the distance on the frequency axis) prominent peaks or fused peaks. Also in this case, as in the fusion of nearby peaks, the peak powers before and after the fusion are conserved, and the center frequencies of the fused peaks are decided from the center frequencies and powers of all the peaks fused.

Table 3 shows the result D9 obtained as described above. As shown in Table 3, the number of the finally obtained peaks is 14. Meanwhile, in Table 3, the common logarithmic values of respective peak powers are added.

TABLE 3

Series of dominant peaks obtained by fusion of slight peaks

| No. | Frequency (Hz) | Power | Common Logarithm |
|---|---|---|---|
| 1 | | | |
| 2* | 2.133 | 0.8714 | −0.0598 |
| 3 | | | |
| 4 | | | |
| 5* | 4.247 | 24.7669 | 1.3939 |
| 6 | | | |
| 7* | 6.420 | 1.0380 | 0.0162 |
| 8 | | | |
| 9 | | | |
| 10* | 8.532 | 0.3619 | −0.4414 |
| 11 | | | |
| 12 | | | |
| 13* | 10.674 | 0.1354 | −0.8685 |
| 14 | | | |
| 15 | | | |
| 16* | 12.794 | 0.0734 | −1.1341 |
| 17 | | | |
| 18 | | | |
| 19* | 14.914 | 0.0360 | −1.4432 |
| 20 | | | |
| 21 | | | |
| 22* | 17.055 | 0.0205 | −1.6892 |
| 23 | | | |
| 24 | | | |
| 25* | 19.182 | 0.0109 | −1.9611 |
| 26 | | | |
| 27 | | | |
| 28* | 21.324 | 0.0062 | −2.2108 |
| 29 | | | |
| 30 | | | |
| 31* | 23.446 | 0.0034 | −2.4698 |
| 32 | | | |
| 33 | | | |
| 34* | 25.572 | 0.0019 | −2.7238 |
| 35 | | | |
| 36 | | | |
| 37* | 27.697 | 0.0011 | −2.9755 |
| 38 | | | |
| 39 | | | |
| 40* | 29.820 | 0.0006 | −3.2330 |

Subsequently, from the fourteen dominant peaks (fused peaks and non-fused prominent peaks) obtained as described above, the gradient is obtained. The trend line, gradient and y-intercept obtained for the set of (frequencies and common logarithmic values of powers) of the fourteen peaks by the linear least squares method are as shown in Table 4.

TABLE 4

Gradient and y-intercept of trend line

| Gradient | y-intercept |
|---|---|
| −0.14201 | 0.855948 |

Then, at the step S13b, the series of the peaks of Table 1 are divided by the respectively corresponding values of the trend line at the respective peak frequency positions, to obtain a series of trend line relative peak powers. In this case, it should be noted that the trend line of Table 4 is a straight line on a semilogarithmic graph and therefore that the respective peak powers should be divided by the respectively corresponding values obtained by multiplying the values of the trend line at the peak center frequencies by any power of 10. Table 5 corresponds to the result D9. In the result of Table 5, calculation is performed for not only the prominent peaks but also for the nearby peaks and slight peaks.

TABLE 5

Relative powers (ratios), integrated ratios and percentages of Respective peaks

| Frequency (Hz) | Power | Trend line | Ratio | Integrated ratio | Percentage |
|---|---|---|---|---|---|
| 0.872 | 0.000289 | 5.3957 | 0.0001 | 0.0001 | 0.0002 |
| 2.114 | 0.852193 | 3.5949 | 0.2371 | 0.2371 | 0.9368 |
| 3.002 | 0.018925 | 2.6894 | 0.0070 | 0.2441 | 0.9646 |
| 3.449 | 0.031369 | 2.3233 | 0.0135 | 0.2577 | 1.0179 |
| 4.248 | 24.731433 | 1.7892 | 13.8227 | 14.0804 | 55.6297 |
| 5.315 | 0.004076 | 1.2622 | 0.0032 | 14.0836 | 55.6425 |
| 6.419 | 1.013633 | 0.8799 | 1.1520 | 15.2356 | 60.1939 |
| 6.647 | 0.024366 | 0.8167 | 0.0298 | 15.2654 | 60.3117 |
| 7.520 | 0.000651 | 0.6138 | 0.0011 | 15.2665 | 60.3159 |
| 8.532 | 0.360084 | 0.4408 | 0.8169 | 16.0834 | 63.5432 |
| 8.914 | 0.001146 | 0.3891 | 0.0029 | 16.0863 | 63.5549 |
| 9.676 | 0.000280 | 0.3032 | 0.0009 | 16.0872 | 63.5585 |
| 10.671 | 0.132703 | 0.2191 | 0.6058 | 16.6930 | 65.9518 |
| 10.946 | 0.002369 | 0.2002 | 0.0118 | 16.7048 | 65.9986 |
| 11.795 | 0.000148 | 0.1517 | 0.0010 | 16.7058 | 66.0024 |
| 12.794 | 0.072841 | 0.1094 | 0.6656 | 17.3715 | 68.6323 |
| 13.164 | 0.000441 | 0.0969 | 0.0046 | 17.3760 | 68.6503 |
| 13.961 | 0.000084 | 0.0747 | 0.0011 | 17.3771 | 68.6547 |
| 14.914 | 0.035796 | 0.0547 | 0.6544 | 18.0315 | 71.2400 |
| 15.347 | 0.000163 | 0.0475 | 0.0034 | 18.0349 | 71.2536 |
| 16.002 | 0.000058 | 0.0383 | 0.0015 | 18.0364 | 71.2595 |
| 17.055 | 0.020247 | 0.0272 | 0.7455 | 18.7819 | 74.2049 |
| 17.454 | 0.000149 | 0.0238 | 0.0063 | 18.7882 | 74.2296 |
| 18.186 | 0.000038 | 0.0188 | 0.0020 | 18.7902 | 74.2376 |
| 19.182 | 0.010827 | 0.0135 | 0.7992 | 19.5894 | 77.3950 |
| 19.626 | 0.000072 | 0.0117 | 0.0062 | 19.5955 | 77.4194 |
| 20.290 | 0.000025 | 0.0094 | 0.0026 | 19.5982 | 77.4297 |
| 21.322 | 0.006025 | 0.0067 | 0.8955 | 20.4936 | 80.9675 |
| 21.657 | 0.000104 | 0.0060 | 0.0173 | 20.5109 | 81.0357 |
| 22.456 | 0.000018 | 0.0046 | 0.0038 | 20.5147 | 81.0508 |
| 23.446 | 0.003333 | 0.0034 | 0.9920 | 21.5067 | 84.9699 |
| 23.845 | 0.000039 | 0.0029 | 0.0134 | 21.5200 | 85.0227 |
| 24.553 | 0.000011 | 0.0023 | 0.0046 | 21.5246 | 85.0409 |
| 25.573 | 0.001856 | 0.0017 | 1.1075 | 22.6321 | 89.4165 |
| 25.992 | 0.000022 | 0.0015 | 0.0149 | 22.6470 | 89.4753 |
| 26.707 | 0.000007 | 0.0012 | 0.0062 | 22.6533 | 89.4999 |
| 27.699 | 0.001040 | 0.0008 | 1.2433 | 23.8966 | 94.4122 |
| 28.163 | 0.000011 | 0.0007 | 0.0149 | 23.9115 | 94.4712 |
| 28.816 | 0.000004 | 0.0006 | 0.0077 | 23.9192 | 94.5016 |
| 29.827 | 0.000580 | 0.0004 | 1.3917 | 25.3109 | 100.0000 |

The inventor has introduced three novel characteristic quantities called $RSEF^{25}$, RSMF and $RSEF^{75}$. These are obtained as the frequencies at which the percentages of Table 5 exceed 25%, 50% and 75% respectively. From Table 5, the frequencies are 4.2 Hz, 4.2 Hz and 19.1 Hz. Thus, the frequencies at which the integrated relative power values correspond to ¼, ½ and ¾ of the total integrated value are obtained as result D10. Since the relative peak powers discretely and locally exist on the frequency axis, it can happen that the value 4.2 Hz of $RSEF^{25}$ becomes equal to that of RSMF.

It is important the novel characteristic quantities $RSEF^{25}$, RSMF and $RSEF^{75}$ are calculated by using the peaks and peak powers discretely existing on the frequency axis as described above. On the other hand, the old characteristic quantities SMF and $SEF^{90}$ are calculated for the spectrum continuously varying on the frequency axis.

Meanwhile, the essential matter in the above processing is the procedure for obtaining the series of the dominant peaks (fused peaks and non-fused prominent peaks in this case) for obtaining the trend line and the powers of the peaks. The inventor analyzed numerous electroencephalogram time series and also chaotic model time series of Roessler, Duffing, Lorenz, etc., and as a result, found that locally prominent peaks appear almost uniformly side by side over the entire frequency bands in these spectra, and has established the abovementioned procedure on the basis of this finding.

For example, if attention is paid to peak No. 3 and peak No. 40 in Table 1, peak No. 3 is called a slight peak, and peak No. 40 is called a prominent peak, in this procedure. However, the power of peak No. 3 is larger. A slight peak, the power of which is slight compared with the nearest locally prominent peak, is called a slight peak. If prominent peaks and slight peaks are identified in this way, the locally dominant peaks distributed almost equally in the entire frequency band up to 30 Hz can be taken out.

An analysis example of this invention is explained below.

At first, four types of electroencephalogram data obtained during rest with closed eyes, sound sleep, arousal and anesthesia were analyzed. For relatively easy analysis, after the optimum segment lengths and the optimum lag values for the respective types of data were examined, a segment data length of 3 seconds and a lag value of 70% were selected as the values satisfying all the types of data and consistently employed for analysis. Meanwhile, even if different segment data lengths and different lag values are used for the respectively types of data, the following conclusion remain positive if they are optimum segment lengths and optimum lag values for the respective types of data.

Figure 11:
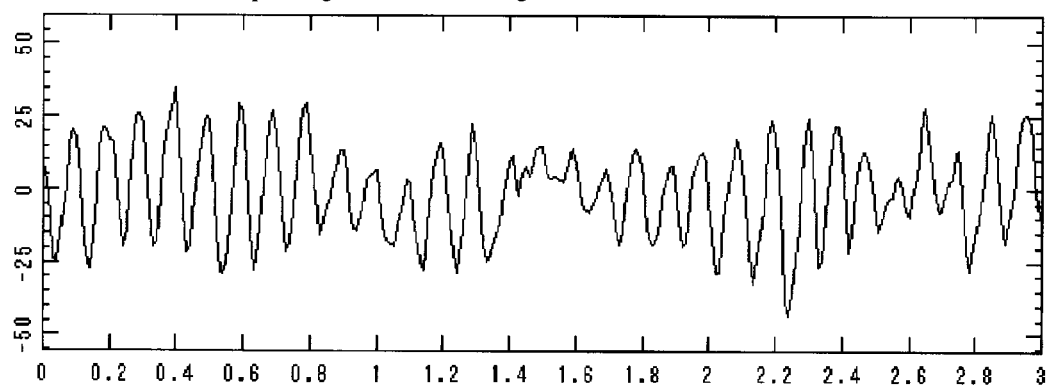
FIG. 11 is diagrams showing electroencephalogram data and MEM-PSDs thereof during rest with closed eyes an example.
Figure 11:
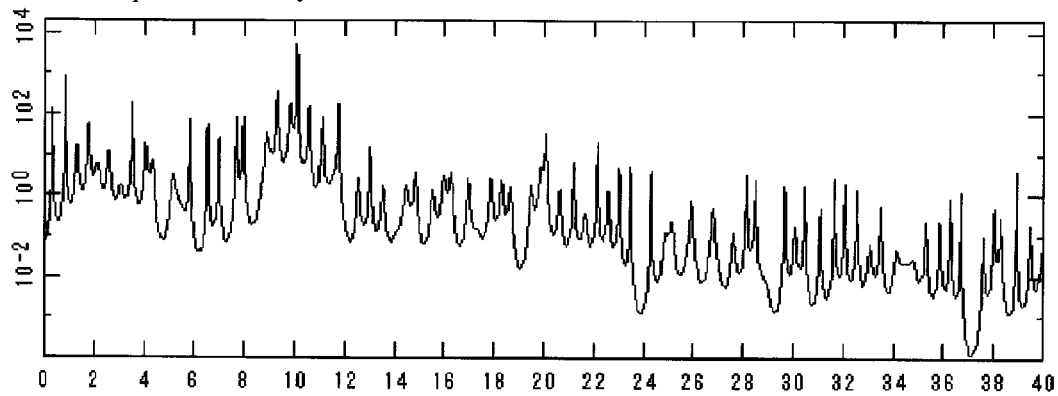
Figure 12:
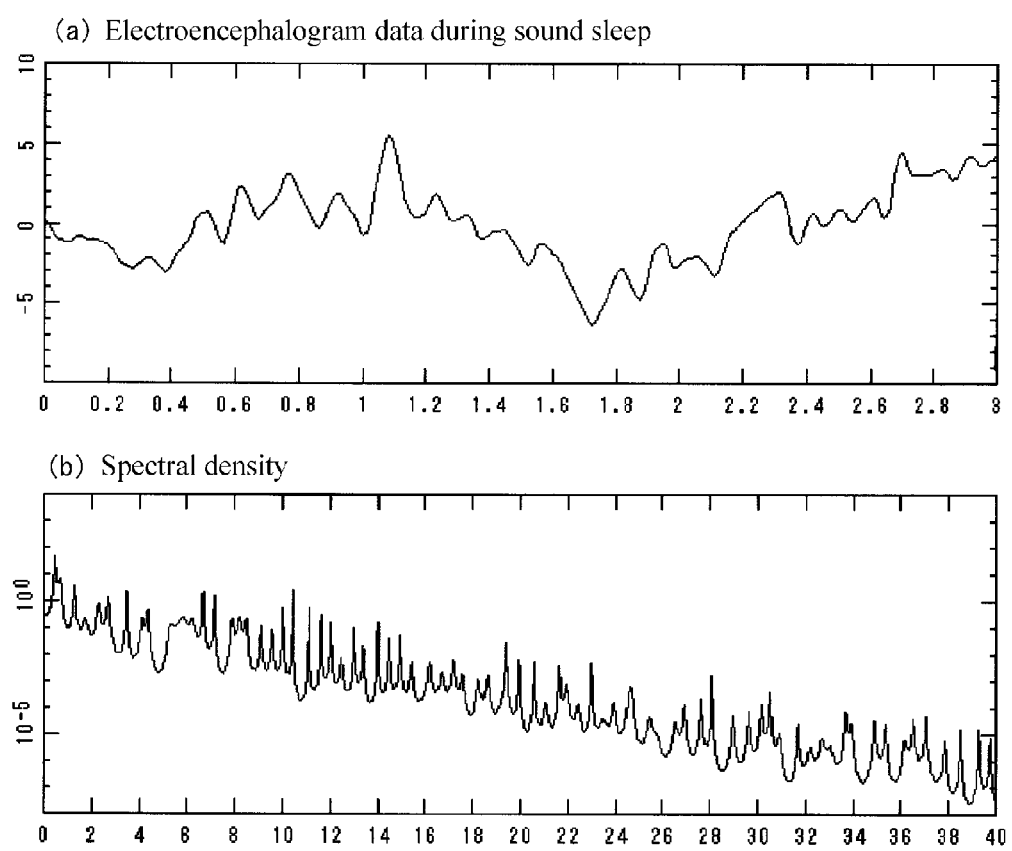
FIG. 12 is diagrams showing electroencephalogram data and MEM-PSDs thereof during sound sleep as an example.

FIGS. 11(a) shows the electroencephalogram data during rest with closed eyes, and (b), the MEM-PSDs thereof. Further, FIGS. 12(a) shows the electroencephalogram data during sound sleep (sleep stage 3 or 4), and (b), the MEM-PSDs thereof.

Figure 13:
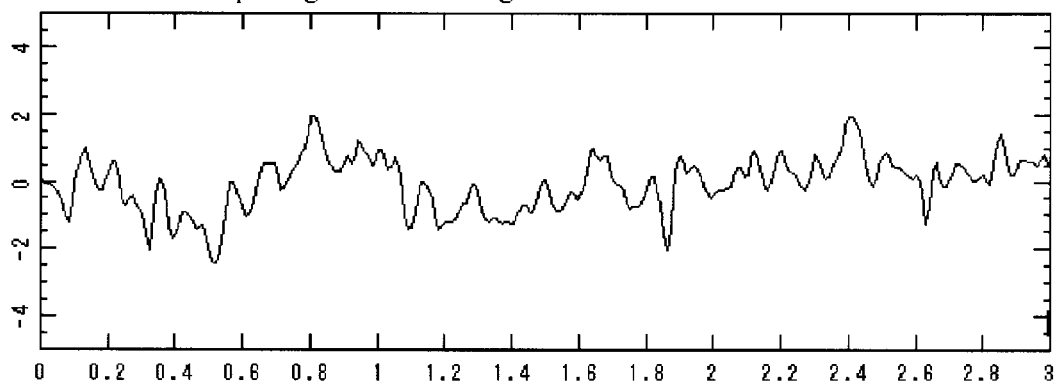
FIG. 13 is diagrams showing electroencephalogram data and MEM-PSDs thereof during arousal as an example.
Figure 13:
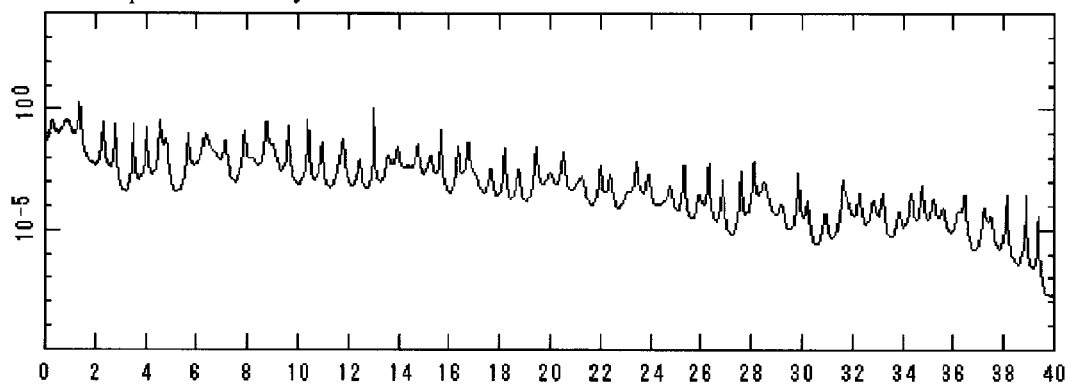
Figure 14:
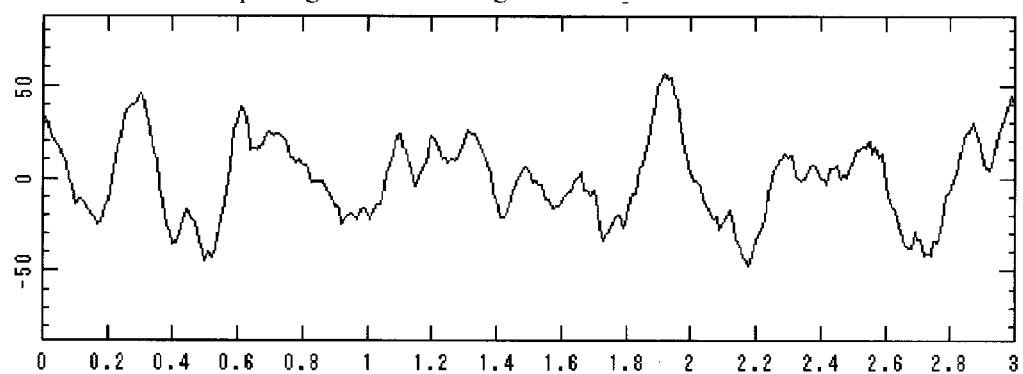
FIG. 14 is diagrams showing electroencephalogram data and MEM-PSDs thereof during anesthesia as an example.
Figure 14:
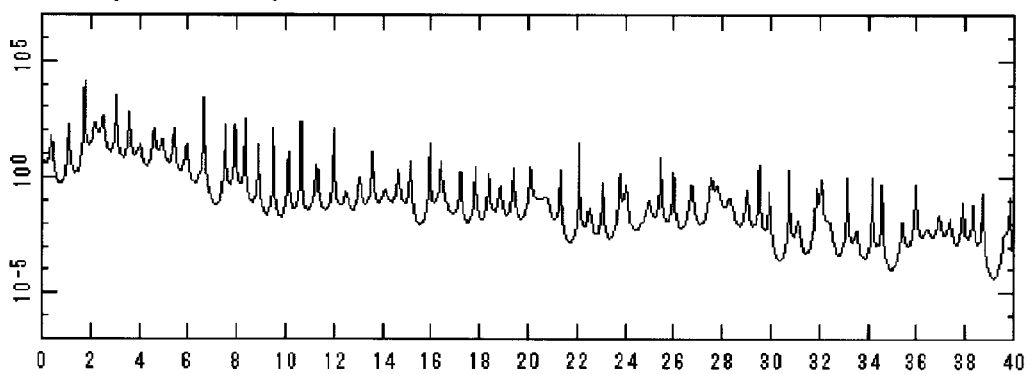

Furthermore, FIGS. 13(a) shows the electroencephalogram data during arousal, and (b), the MEM-PSDs thereof, and FIGS. 14(a) shows the electroencephalogram data during anesthesia, and (b), the MEM-PSDs thereof.

Moreover, Table 6 lists the results of analysis by this invention.

TABLE 6

|  | Rest with closed eyes | Sound sleep | Arousal | Anesthesia |
|---|---|---|---|---|
| Overall trend of spectrum | −0.060 | −0.170 | −0.070 | −0.194 |
| RSMF | 10.0 Hz | 17.7 Hz | 13.8 Hz | 6.6 Hz |
| $RSEF^{75}$-$RSEF^{25}$ | 0.1 Hz | 12.8 Hz | 11.2 Hz | 10.1 Hz |
| $RSEF^{25}$ | 10.0 Hz | 10.2 Hz | 8.8 Hz | 3.0 Hz |
| $RSEF^{75}$ | 10.1 Hz | 23.0 Hz | 20.0 Hz | 13.1 Hz |
| δ(1~4 Hz) | 7.1% | 57.3% | 46.1% | 83.4% |
| θ(4~8 Hz) | 5.7% | 31.3% | 21.2% | 13.8% |
| α(8~13 Hz) | 83.0% | 10.0% | 20.3% | 2.2% |
| β(13~30 Hz) | 4.1% | 1.1% | 12.3% | 0.6% |
| SMF | 10.1 Hz | 3.3 Hz | 4.6 Hz | 2.5 Hz |
| $SEF^{90}$-SMF | 0.9 Hz | 4.9 Hz | 9.1 Hz | 3.1 Hz |
| $SEF^{90}$ | 11.0 Hz | 8.2 Hz | 13.7 Hz | 5.6 Hz |

* The totals of the percentages of the powers of frequencies δ to β are not necessarily 100% respectively because of fractions processed.

The "Overall trend of spectrum," "RSMF," "$RSEF^{75}$-$RSEF^{25}$," "$RSEF^{25}$" and "$RSEF^{75}$" in the upper five lines of this table are the analytical quantities especially characterizing the analyzer of this invention. Further, such quantities as "SMF" and "$SEF^{90}$" calculated from the highly precise MEM-PSDs of the analyzer of this invention are also useful. As described above, in this invention, it can be expected that segment data is an output from a certain system (brain) in the same state. Therefore, all the characteristic quantities can be evaluated as values accurately reflecting the state of the system.

With regard to the results of the electroencephalogram data analysis during rest with closed eyes, first of all, the overall trend of the spectrum is as gentle as −0.060. RSMF is 10.0 Hz, and the center of the relative peak power string is positioned in a band (8 to 13 Hz). Further, near this center frequency, 50% of relative peak powers are concentrated in a width of 0.1 Hz (the value of $RSEF^{75}$-$RSEF^{25}$). If it is assumed that relative peak powers are equally distributed in the entire frequency band (1 to 30 Hz), since the value of $RSEF^{75}$-$RSEF^{25}$ is 14.5 Hz, the value of 0.1 Hz width means that relative powers are concentrated near the center frequency during rest with closed eyes. SMF is 10.1 Hz and $SEF^{90}$ is 11.0 Hz. The difference between both is as slight as 0.9 Hz, and it can be seen that α peak bears almost all the power. The power of a frequency band corresponds to 83% of the total power (of 1 to 30 Hz), being prominent compared with the values of frequency bands δ, θ and β.

On the other hand, during the sound sleep determined to be sleep stage 3 or 4, the overall trend of the spectrum is as sharp as −0.170. RSMF is 17.7 Hz and $RSEF^{75}$-$RSEF^{25}$ is 12.8 Hz. These values indicate that the relative peaks are almost uniformly distributed over the entire frequency band (1 to 30 Hz). That is, on the sharp spectral gradient, many spectral peaks appear side by side without any prominent peak. Since the overall trend of the spectrum is sharp, SMF is 3.3 Hz being on the low frequency side. Further, the power ratios of frequency bands δ, θ, α and β are respectively 57.3%, 31.3%, 10.0% and 1.1%, showing a sharp decline in the ascending order of frequency.

So, whether or not the state of rest with closed eyes can be distinguished from the state of arousal is discussed below. In Table 6, the overall trend of the spectrum of the electroencephalogram data obtained during arousal is as gentle as −0.070, being close to the value of −0.060 during rest with closed eyes. On the other hand, $RSEF^{75}$-$RSFE^{25}$ is 11.2 Hz, a value observed in the case where the relative peaks are uniformly distributed in the entire frequency band, being quite different from the value of 0.1 Hz during rest with closed eyes. That is, both the states can be clearly distinguished from each other. This can be seen also from the power ratios of the frequency bands δ to β. In the state of arousal, the power ratio of frequency band θ is almost equal to the power ratio of frequency band α, but the divisional power gradually declines in the order of frequency bands δ to β in contrast to the state of rest with closed eyes where the power ratio of frequency band a is prominent. In the state of arousal, SMF is 4.6 Hz being on the low frequency side, and the difference between $SEF^{90}$ and SMF is 9.1 Hz, being clearly different from the value of 0.9 Hz in the state of rest with closed eyes.

On the other hand, the overall trend of electroencephalogram data during anesthesia is as sharp as −0.194, and RSMF is 6.6 Hz while $RSEF^{75}$-$RSEF^{25}$ is 10.1 Hz. Comparing with the data during sound sleep also with a sharp gradient (−0.170), RSMF is 6.6 Hz being remarkably on the low frequency side characteristically, compared with 17.7 Hz during sound sleep. Further, the power ratio of frequency band δ is as prominent as 83.4%, and SMF is as small as 2.5 Hz. This trend during anesthesia is similar to that during sound sleep. That is, the largest difference between the electroencephalogram during anesthesia and that during sound sleep can be found in RSMF.

Figure 15:
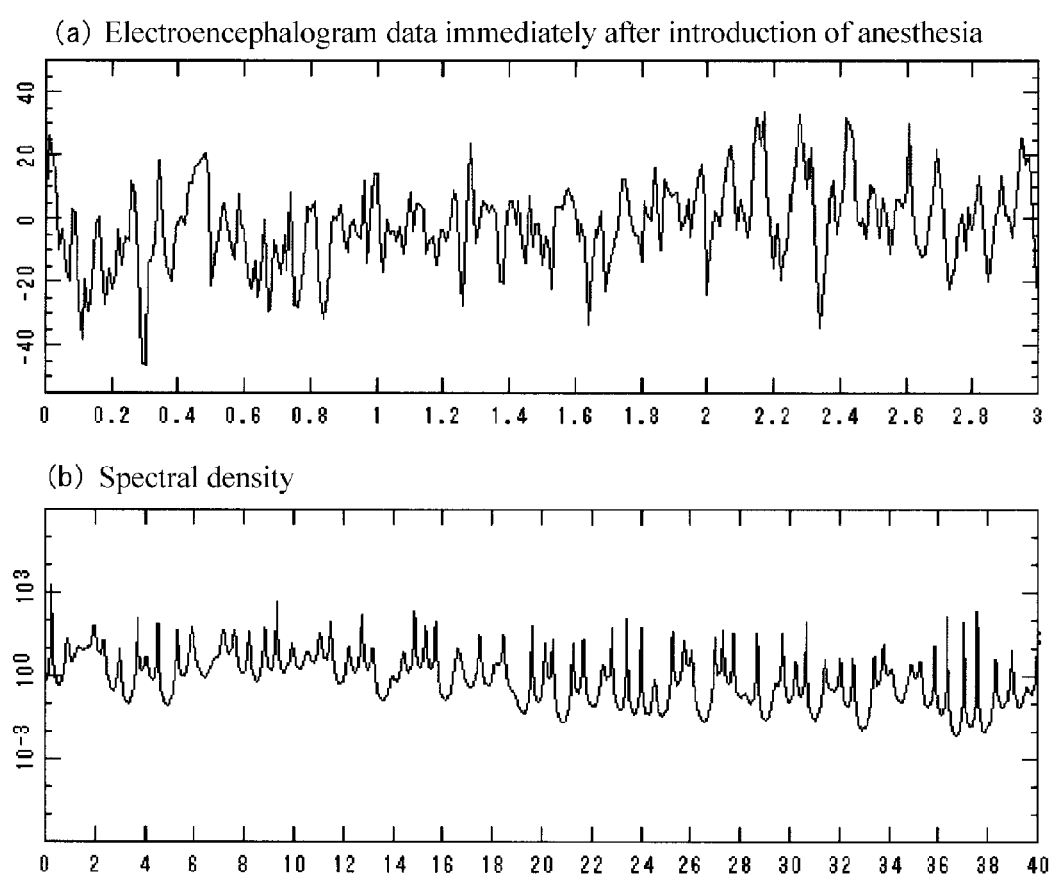
FIG. 15 is diagrams showing electroencephalogram data and MEM-PSDs thereof immediately after introduction of anesthesia as an example.
Figure 16:
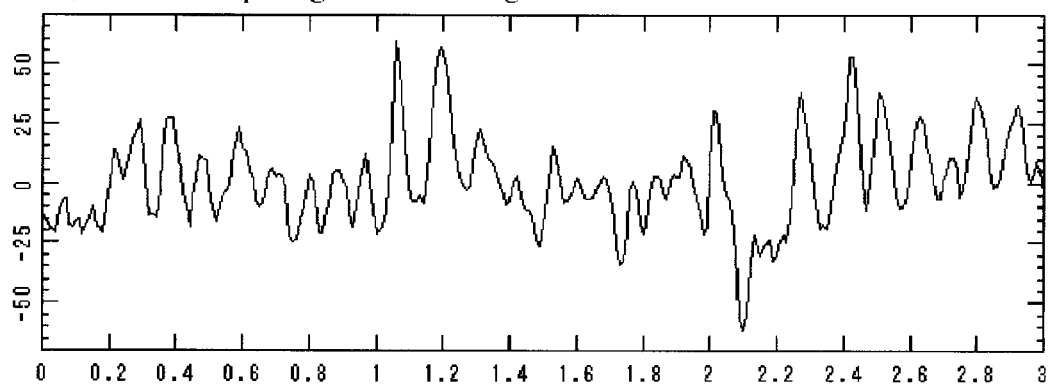
FIG. 16 is diagrams showing electroencephalogram data and MEM-PSDs thereof during introduction of anesthesia as an example.
Figure 16:
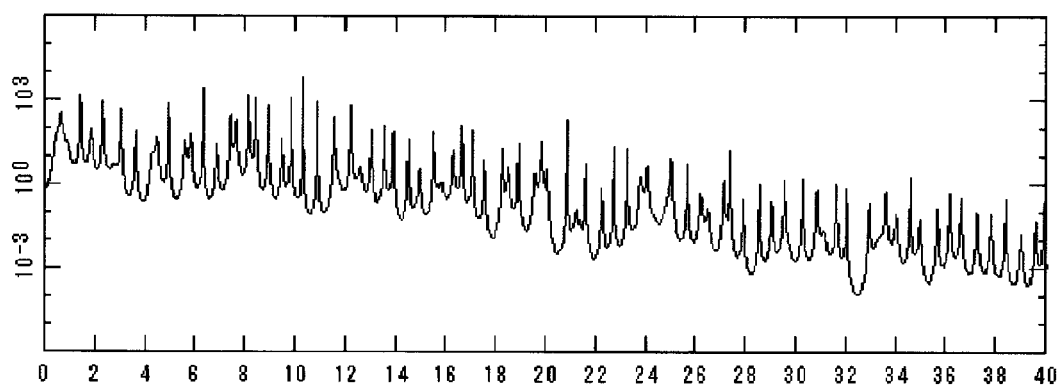

Next, whether the change in response to the degree of anesthesia after introduction of anesthesia can be identified from these characteristic quantities is discussed below. Additional analysis was performed for confirming it. FIG. 15 shows the data immediately after introduction of anesthesia, and FIG. 16 shows the data during introduction of anesthesia. In FIGS. 15 and 16, each (a) shows electroencephalogram data, and (b), the MEM-PSDs thereof. These data are followed by the abovementioned electroencephalogram data during anesthesia shown in FIG. 14.

Table 7 lists the results of analysis performed by the analyzer of this invention, showing the data obtained with the anesthetic depth gradually increased from immediately after introduction of anesthesia in the second column to the state of anesthesia in the fourth column.

TABLE 7

|  | Immediately after introduction of anesthesia | During introduction of anesthesia | In the state of anesthesia |
| --- | --- | --- | --- |
| Overall trend of spectrum | −0.020 | −0.078 | −0.194 |
| RSMF | 12.7 Hz | 11.5 Hz | 6.6 Hz |
| $RSEF^{75}$-$RSEF^{25}$ | 8.6 Hz | 12.6 Hz | 10.1 Hz |
| $RSEF^{25}$ | 8.8 Hz | 8.2 Hz | 3.0 Hz |
| $RSEF^{75}$ | 17.4 Hz | 20.8 Hz | 13.1 Hz |
| δ(1~4 Hz) | 18.4% | 30.4% | 83.4% |
| θ(4~8 Hz) | 18.1% | 23.8% | 13.8% |
| α(8~13 Hz) | 31.0% | 38.1% | 2.2% |
| β(13~30 Hz) | 32.4% | 7.5% | 0.6% |
| SMF | 9.5 Hz | 7.6 Hz | 2.5 Hz |
| $SEF^{90}$-SMF | 23.3 Hz | 4.7 Hz | 3.1 Hz |
| $SEF^{90}$ | 22.8 Hz | 12.3 Hz | 5.6 Hz |

With regard to Table 7, at first, the overall trend of the spectrum gradually increased from −0.020 immediately after introduction of anesthesia to −0.078 during introduction of anesthesia, and finally sharply to −0.194 in the state of anesthesia.

In contrast to the change in the overall trend of the spectrum, the analysis results of RSMF and $RSEF^{75}$-$RSEF^{25}$ are characteristic. RSMF showed a large value of 12.7 Hz immediately after introduction of anesthesia, and showed 11.5 Hz during introduction of anesthesia and a low frequency of 6.6 Hz in the state of anesthesia. $RSEF^{75}$-$RSEF^{25}$ remained almost constant at 8.6 Hz, 12.6 Hz and 10.1 Hz. That is, the relative peak string was distributed equally in the entire frequency band immediately after introduction of anesthesia, and RSMF moved toward the low frequency side in the state of sufficient anesthesia.

On the other hand, items δ to $SMF^{90}$ not standardized by the trend (curve) line changed in behavior depending on the degree of anesthesia. SMF moved from 9.5 Hz after introduction of anesthesia to 7.6 Hz and 2.5 Hz gradually toward the low frequency side. Further, $SEF_{90}$ also moved toward the low frequency side successively, to finally reach 5.6 Hz in the state of anesthesia. These changes can be considered to reflect the change in the overall trend of the spectrum.

Similarly also with regard to the power ratios of frequency bands δ to β, as can be estimated from the change in the overall trend of the spectrum, the state of having dominant power near the frequency band α changed to the state of having predominant power in the frequency band δ.

From the above, it can be seen that the analyzer of this invention allows the respective states of rest with closed eyes, arousal, sound sleep and anesthesia to be identified from the electroencephalogram data and also allows the changes with the lapse of time after introduction of anesthesia to be accurately identified.

This invention as described above is different from the analyzer of the conventional method in the following matters.
1. Segment Data to be Analyzed
(Present Invention)

Data with a length of 2 to 5 seconds expected to remain in the same state. Variable length or fixed length also possible. In the case of a fixed length, a series of optimum segment lengths is examined beforehand, to set a shorter length.

(Conventional Method)

Data with a length of data points as many as any power of 2 decided by the sampling frequency and the analysis method (FFT). Fixed length.

2. Spectrum Calculation Method (Present Invention)

Maximum entropy method (MEM). Since MEM is employed, the segment length (number of data points) can be set as desired.

(Conventional Method)

FFT. Because of a high speed method using data with an infinite length, many false peaks attributable to the segment length are contained inevitably in a spectrum.

3. Method for Calculating the Overall Trend of an Exponential Spectrum

The gradient produced by series of center frequencies and peak powers of the dominant peaks of the MEM-PSDs obtained from the optimum segment length and the optimum lag value is obtained. As described above, it corresponds to obtaining the overall trend of the frequency distribution of the powers of the respective terms in the case where segment data is described by a generalized trigonometric polynomial by the optimization of the segment length and the lag value.

(Conventional Method)

The processing is not mounted, or the gradient is obtained from all the peak points including the false peaks attributable to the segment length or from all the calculation points.

4. Extracted Other Characteristic Quantities of Electroencephalogram Spectrum (Present Invention)

The characteristic quantities include all the characteristic quantities obtained by the conventional method. In addition, the relative peak power string standardized by the trend (curve) line of an exponential spectrum, including $RSEF^{25}$ (Relative Spectral Edge Frequency 25) frequency at which the integrated value of relative peak powers corresponds to ¼ of the total integrated value, RSMF (Relative Spectral Mid Frequency) frequency at which the integrated value corresponds to ½, and $RSEF^{75}$ frequency at which the integrated value corresponds to ¾. These three quantities have been introduced in this invention and correspond to the integrated values of the powers of the respective terms of the generalized trigonometric polynomial describing the segment data.

(Conventional Method)

Divisional powers of frequency bands $\delta$, $\theta$, $\alpha$ and $\beta$ (1 to 4 Hz, 4 to 8 Hz, 8 to 13 Hz and 13 to 30 Hz), SMF (Spectral Mid Frequency, the frequency at which the integrated value of the spectrum corresponds to 50% in 1 to 30 Hz), and $SEF^{90}$ (Spectral Edge Frequency, the frequency at which the integrated value of the spectrum corresponds to 90%).

Further, this invention has the following features in comparison with the conventional method owing to the above-mentioned differences.

(1) Since the electroencephalogram data of the optimum segment length is handled, it can be expected that the "dynamically stable data" estimated to be always in a certain dynamic state is analyzed.

(2) In addition, since the spectrum is calculated with the optimum lag value, it can be expected that the obtained MEM-PSDs correspond to the generalized trigonometric polynomial expression of the original segment data. That is, it can be expected that the behavior of the electroencephalogram data on the time base is consistent with the behavior of the MEM-PSDs on the frequency axis.

(3) As a result of the consistency secured as described above, the respective quantities such as the overall trend of the obtained spectrum and divisional powers are more reliable than those obtained by using the conventional method.

(4) In addition to the quantities obtained by the conventional electroencephalogram analysis, the most basic features of the spectrum in this invention are described not only as the overall trend of the trend (curve) line but also as the set consisting of the gradient and the respective quantities produced by the relative peak string (the frequencies at which the integrated value of the relative peak powers corresponds to ¼, ½ or ¾). Therefore, findings concerning the dynamic state of a system (brain) that could not be identified by the conventional method can be obtained.

DESCRIPTION OF THE SYMBOLS

1:Time series data
2:Segment condition input section
3:Analysis condition input section
4:Optimum analysis condition deriving section
5:Analysis execution section
6:Setting processing means
7:First processing means
8:Second processing means
9:Third processing means
10:Segment preparation means
11:Power spectral density calculation means
12:Peak extraction means
13:Characteristic quantity extraction means

What is claimed is:

1. A time series data analyzer for analyzing the segments obtained from time series data, comprising:
a non-transitory memory device storing a program; and
a processor that executes the program, which causes the time series data analyzer to operate as:
a segment condition input section, into which a shortest segment length, a longest segment length and a total number of obtained segments including the shortest segment, the longest segment and other segments are input as input items, the other segments being segments with different lengths ranging from the shortest segment length to the longest segment length or located at each time step between the shortest segment and the longest segment,
an analysis condition input section, into which a minimum lag value, a maximum lag value, and intervals for setting a series of lag values between the minimum lag value and the maximum lag value are inputted as input items,
an optimum analysis condition deriving section, in which each segment is analyzed based on segment conditions inputted in the segment condition input section and analysis conditions inputted in the analysis condition input section from all analysis conditions using a maximum entropy method and a nonlinear least squares method, for selecting one appropriate segment and one appropriate analysis condition from all analysis results as a selected result and deriving an optimum segment length and an optimum lag value as optimum analysis conditions in correspondence to the selected result, and
an analysis execution section, in which the optimum analysis conditions derived by the optimum analysis condition deriving section are set as analysis conditions, for executing an analysis by the maximum entropy method.

2. A time series data analyzer according to claim 1, wherein the optimum analysis condition deriving section comprises:
a setting processing means for obtaining multiple segments different in length from the time series data based on the conditions inputted in the segment condition input section, to set the segments as sample segments and for reading the analysis conditions inputted in the analysis condition input section, to set the analysis conditions;

a first processing means for calculating power spectral densities for each of the sample segments set by the setting processing means, under all analysis conditions using the maximum entropy method;

a second processing means for extracting dominant spectral peaks for the respective power spectral densities obtained by the first processing means, and calculating respective quantities of trigonometric polynomial expressions for the sample segments from the dominant spectral peaks by the nonlinear least squares method; and a third processing means for determining validity of the trigonometric polynomial expressions obtained by the second processing means for the sample segment data and consistency of the trigonometric polynomial expressions for the power spectral densities, and selecting one sample segment corresponding to a trigonometric polynomial expression having a specified validity and consistency, for deriving a segment length and a lag value corresponding to the sample segment as optimum segment length and the optimum lag value.

3. A time series data analyzer according to claim 2, wherein the second processing means extracts a number of the dominant spectral peaks, and respective peak frequencies and peak powers of the dominant spectral peaks from the power spectral densities calculated by the first processing means, to calculate the respective quantities of the trigonometric polynomial expressions by calculation of the nonlinear least squares method for minimizing sum of squares of residuals, with the number of the dominant spectral peaks being the number of terms and the inverse numbers of the respective peak frequencies as the initial values of the periods of respective trigonometric terms, and wherein the third processing means includes:

a first selection function for comparing standard deviations of residuals in the respective quantities of the trigonometric polynomial expressions concerning the respective sample segments, with a set value, to reject the trigonometric polynomial expressions, the standard deviations of which not being lower than a set value and retaining other trigonometric polynomial expressions as selection candidates, a second selection function for comparing periods of respective terms of polynomials decided by the nonlinear least squares method with initial values of periods set from inverse numbers of peak frequencies of power spectral densities, to reject the trigonometric polynomial expressions, for which differences obtained as results of the comparison are not lower than a set value, and to retain the other trigonometric polynomial expressions as selection candidates, and a third selection function for comparing powers obtained from the amplitudes of the respective terms of the polynomials decided by the nonlinear least squares method, with the powers of peaks corresponding to power spectral densities pair by pair, to reject the trigonometric polynomial expressions having the amplitudes, the differences of which obtained as results of the comparison are not lower than a set value, and to retain the other trigonometric polynomial expressions as selection candidates, wherein the processings by the first, second and third selection functions are performed one after another for selecting the trigonometric polynomial expression(s) high in validity and consistency.

4. A time series data analyzer according to claim 3, wherein the third processing means has a fourth selection function for selecting a trigonometric polynomial expression that is smallest in the standard deviation of residuals in the case where multiple trigonometric polynomial expressions remain as selection candidates after performing the processings by the first, second and third selection functions one after another.

5. A time series data analyzer according to claim 3, wherein the third processing means has a fifth selection function for selecting the longest sample segment as the optimum sample segment in the case where multiple sample segments having the selected trigonometric polynomial expression remain after performing the processings by the first, second and third selection functions to ensure that the sample segment selected by the fifth selection function can be selected as the optimum segment and that the lag value used for calculating the power spectral densities in correspondence to the selected trigonometric polynomial expression can be selected as the optimum lag value for the sample segment.

6. A time series data analyzer according to claim 4, wherein the third processing means has a fifth selection function for selecting the longest sample segment as the optimum sample segment in the case where multiple sample segments having the selected trigonometric polynomial expression remain after performing the processings by the first, second, third and fourth selection functions, to ensure that the sample segment selected by the fifth selection function can be selected as the optimum segment and that the lag value used for calculating the power spectral densities in correspondence to the selected trigonometric polynomial expression can be selected as the optimum lag value for the sample segment.

7. A time series data analyzer according to claim 1, wherein the analysis execution section comprises:

a segment preparation means for obtaining segments from the time series data based on the optimum segment length derived by the optimum analysis condition deriving section and set in an analysis condition setting means;

a power spectral density calculation means for calculating the power spectral densities for the prepared segments by the maximum entropy method using the optimum lag value derived by the optimum analysis condition deriving section and set in the analysis condition setting means;

a peak extraction means for extracting the number of dominant peaks of the calculated power spectral densities, and center frequencies and peak powers of the respective peaks; and a characteristic quantity extraction means for extracting characteristic quantities from an extracted peak string.

8. A time series data analyzer according to claim 7, wherein the peak extraction means extracts dominant peaks by a first processing of obtaining a first local peak in each range having as width at least three times the average interval between peaks obtained from all the peaks of power spectral densities, and fusing the obtained local peak with any adjacent peak within each interval shorter than the average interval thereby forming a first fused peak, and by a second processing of fusing all the peaks other than the first local peak and the first fused peak with the nearest second local peak or second fused peak respectively, wherein in the case where multiple peaks are fused, the peak powers prevailing before and after the fusion are conserved, and a center frequency of each fused peak is obtained in proportion to the peak powers of the multiple peaks existing before the fusion.

9. A time series data analyzer according to claims 7, wherein the characteristic quantity extraction means comprises:
a trend line calculation means for obtaining a gradient and a y-intercept of a trend line of an exponential spectrum by the linear least squares method for a set of logarithmic peak power values and peak frequencies of the multiple dominant peaks extracted by the peak extraction means;
a relative power calculation means for obtaining relative power by dividing the peak power values of all the peaks obtained by the power spectral density calculation means, by the power values shown by the trend line, for normalization, and
a characteristic quantity calculation means for calculating characteristic quantities of the relative peak power distribution from the peaks discretely arranged on the frequency axis and the relative peak powers thereof.

10. A time series data analyzer according to claim 7, wherein the time series data is electroencephalogram data, and the characteristic quantities extracted by the characteristic quantity extraction means include three frequencies at which an integrated value obtained by integrating the relative peak powers from a low frequency side in the frequency band of interest of an electroencephalogram spectrum ranging from 1 to 30 Hz or 0.5 to 30 Hz corresponds to 25%, 50% or 75% of a total relative peak power of the frequency band of interest.

11. A non-transitory computer-readable recording medium recording a time series data analysis program, for analyzing the segments obtained from time series data, the time series data analysis program causing a computer to perform steps comprising:
a step of inputting a shortest segment length, a longest segment length, and a total number of obtained segments including the shortest segment, the longest segment and other segments as input items, the other segments having different lengths ranging from the shortest segment length to the longest segment length or located at each time step between the shortest segment and the longest segment;
a step of inputting a minimum lag value, a maximum lag value, and intervals for setting the series of lag values between the minimum lag value and the maximum lag value, as input items;
a step of analyzing each of the segments based on inputted segment conditions and inputted analysis conditions from all analysis conditions using a maximum entropy method and a nonlinear least squares method, for selecting one appropriate segment and one appropriate analysis condition from all analysis results as a selected result and deriving optimum analysis conditions consisting of an optimum segment length and an optimum lag value in correspondence to the selected result; and
a step of setting the derived optimum analysis conditions as analysis conditions for executing the analysis by the maximum entropy method.

12. A non-transitory computer-readable recording medium recording a time series data analyzing program, according to claim 11, wherein the step of deriving analysis comprises:
a step of obtaining multiple segments different in length from the time series data based on the inputted segment conditions and setting them as sample segments:
a step of setting analysis conditions;
a first processing step of calculating power spectral densities for each of the set sample segments under all the set analysis conditions using the maximum entropy;
a second processing step of extracting dominant spectral peaks for respective power spectral densities obtained by the first processing step, and calculating respective quantities of trigonometric polynomial expressions for the sample segments from the dominant spectral peaks by the nonlinear least squares method; and
a third processing step of determining validity of the trigonometric polynomial expressions obtained by the second processing step for the sample segment data and consistency of the trigonometric polynomial expressions for the power spectral densities and selecting one sample segment corresponding to the trigonometric polynomial expression having a certain validity and consistency, and for deriving the segment length and the lag value corresponding to the selected sample segment, as the optimum segment length and the optimum lag value.

13. A non-transitory computer-readable recording medium recording a time series data analysis program, according to claim 12, wherein
wherein the second processing step includes:
a step of extracting a number of the dominant spectral peaks, and peak frequencies and peak powers of the dominant spectral peaks from the power spectral densities calculated by the first processing step, and
a step of calculating the respective quantities of the trigonometric polynomial expressions by calculation of the nonlinear least squares method for minimizing a sum of squares of residuals, with the number of the dominant spectral peaks as the number of terms, and the inverse numbers of the respective peak frequencies as the initial values of the periods of respective trigonometric terms, and
wherein the third processing step includes:
a first selection step of comparing standard deviations of residuals in the respective quantities of the trigonometric polynomial expressions concerning the respective sample segments, with a set value, to reject the trigonometric polynomial expressions, the standard deviations of which are not lower than the set value and to retain the other trigonometric polynomial expressions as selection candidates,
a second selection step of comparing the periods of the respective terms of the polynomials decided by the nonlinear least squares method, with the initial values of the periods set from inverse numbers of the peak frequencies of power spectral densities, to reject the trigonometric polynomial expressions, for which differences obtained as results of the comparison are not lower than a set value, and to retain the other trigonometric polynomial expressions as selection candidates, and
a third selection step of comparing powers obtained from amplitudes of the respective terms of the polynomials decided by the nonlinear least squares method, with the powers of the peaks corresponding to power spectral densities pair by pair, to reject the trigonometric polynomial expressions having the amplitudes, differences of which obtained as results of the comparison are not lower than a set value, and to retain the other trigonometric polynomial expressions as selection candidates,
wherein the processings by the first, second and third selection steps are performed one after another for selecting the trigonometric polynomial expression(s) high in validity and consistency.

14. A non-transitory computer-readable recording medium recording a time series data analysis program according to claim 13,
wherein the third processing step has a fourth selection step of selecting the trigonometric polynomial expression that is smallest in the standard deviation of residuals in the case where multiple trigonometric polynomial expressions remain as selection candidates after performing the processings by the first, second and third selection steps one after another.

15. A non-transitory computer-readable recording medium recording a time series data analysis program, according to claim 13,
wherein the third processing step has a fifth selection step of selecting a longest sample segment as an optimum sample segment in the case where multiple sample segments having the selected trigonometric polynomial expression remain as selection candidates after performing the processings by the first, second and third selection steps, to ensure that the sample segment selected by the fifth selection step can be selected as an optimum segment and that a lag value used for calculating the power spectral densities in correspondence to the selected trigonometric polynomial expression can be selected as the optimum lag value for the sample segment.

16. A non-transitory computer-readable recording medium recording a time series data analysis program, according to claim 14,
wherein the third processing step has a fifth selection step of selecting a longest sample segment as an optimum sample segment in the case where multiple sample segments having the selected trigonometric polynomial expression remain as selection candidates after performing the processings by the first, second, third and fourth selection steps, to ensure that the sample segment selected by the fifth selection step can be selected as an optimum segment and that a lag value used for calculating the power spectral densities in correspondence to the selected trigonometric polynomial expression can be selected as the optimum lag value for the sample segment.

17. A non-transitory computer-readable recording medium recording a time series data analysis program, according to any one of claims 11, wherein the analysis execution step comprises:
a segment preparation step of obtaining segments from the time series data based on the optimum segment length derived by the optimum analysis condition deriving step and set in an analysis condition setting step,
a power spectral density calculation step of calculating the power spectral densities for the prepared segments by the maximum entropy method using the optimum lag value derived by the optimum analysis condition deriving step and set in the analysis condition setting step,
a peak extraction step of extracting a number of dominant peaks of the calculated power spectral densities, and center frequencies and peak powers of the respective peaks, and
a characteristic quantity extraction step of extracting characteristic quantities from an extracted peak string.

18. A non-transitory computer-readable recording medium recording a time series data analysis program, according to claim 17, wherein the peak extraction step comprises:
a first processing step comprising
a step of obtaining an average interval between peaks from all the peaks of power spectral densities,
a step of obtaining a first local peak in each range having a width at least three times the obtained average interval and
a step of fusing the obtained the first local peak with any adjacent peak within each interval shorter than the average interval for forming a first fused peak, and
a second processing step of fusing all the peaks other than the first local peak and the first fused peak with a nearest second local peak or a second fused peak respectively, wherein
in the first processing step and the second processing step, in the case where multiple peaks are fused, the peak powers prevailing before and after the fusion are conserved, and a center frequency of each fused peak is obtained in proportion to the peak powers of the multiple peaks existing before the fusion.

19. A non-transitory computer-readable recording medium recording a time series data analysis program, according to claim 17, wherein the characteristic quantity extraction step comprises:
a trend line calculation step of obtaining a gradient and a y-intercept of a trend line of an exponential spectrum by the linear least squares method for a set of logarithmic peak power values and peak frequencies of the multiple dominant peaks extracted by the peak extraction step,
a relative power calculation step of obtaining relative power by dividing the peak power values of all the peaks obtained by the power spectral density calculation step, by the power values shown by the trend line, for normalization, and
a characteristic quantity calculation step of calculating characteristic quantities of the relative peak power distribution from the peaks discretely arranged on the frequency axis and the relative peak powers thereof.

20. A non-transitory computer-readable recording medium recording a time series data analysis program, according to claim 17, wherein the time series data is electroencephalogram data, and the characteristic quantities extracted by the characteristic quantity extraction step include three frequencies at which an integrated value obtained by integrating the relative peak powers from a low frequency side in a frequency band of interest of an electroencephalogram spectrum ranging from 1 to 30 Hz or 0.5 to 30 Hz corresponds to 25%, 50% or 75% of a total relative peak power of the frequency band of interest.

* * * * *